United States Patent
Matsuo

(10) Patent No.: US 9,501,704 B2
(45) Date of Patent: Nov. 22, 2016

(54) DROWSINESS ESTIMATION DEVICE, DROWSINESS ESTIMATION METHOD, AND COMPUTER-READABLE NON-TRANSIENT RECORDING MEDIUM

(71) Applicant: Panasonic Intellectual Property Corporation of America, Torrance, CA (US)

(72) Inventor: Masatoshi Matsuo, Fukuoka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 112 days.

(21) Appl. No.: 14/355,078

(22) PCT Filed: Oct. 4, 2013

(86) PCT No.: PCT/JP2013/005924
§ 371 (c)(1),
(2) Date: Apr. 29, 2014

(87) PCT Pub. No.: WO2014/054293
PCT Pub. Date: Apr. 10, 2014

(65) Prior Publication Data
US 2014/0313309 A1    Oct. 23, 2014

(30) Foreign Application Priority Data

Oct. 5, 2012 (JP) ................. 2012-222830

(51) Int. Cl.
*G06K 9/00* (2006.01)
*A61B 5/01* (2006.01)
(Continued)

(52) U.S. Cl.
CPC ......... *G06K 9/00845* (2013.01); *A61B 5/0077* (2013.01); *A61B 5/01* (2013.01);
(Continued)

(58) Field of Classification Search
CPC ............... G06K 9/00845; G06K 9/00604; G06K 9/0061; A61B 5/0077; A61B 5/01; A61B 5/015; A61B 5/18; B60K 28/06

USPC ................. 348/78, 208.14, 576
See application file for complete search history.

(56) References Cited

U.S. PATENT DOCUMENTS 5,689,241 A * 11/1997 Clarke, Sr. ............. G08B 21/06 340/575
2004/0090334 A1 * 5/2004 Zhang ................... G08B 21/06 340/575

(Continued)

FOREIGN PATENT DOCUMENTS

| JP | 5-3876 | 1/1993 |
|---|---|---|
| JP | 9-154835 | 6/1997 |

(Continued)

OTHER PUBLICATIONS

International Search Report issued Jan. 7, 2014 in International (PCT) Application No. PCT/JP2013/005924.

(Continued)

*Primary Examiner* — Thai Tran
*Assistant Examiner* — Nien-Ru Yang
(74) *Attorney, Agent, or Firm* — Wenderoth, Lind & Ponack, L.L.P.

(57) ABSTRACT

A drowsiness estimation device comprises an imaging unit 1, a regional temperature calculation unit 6, and a weighted subtraction unit 7. The imaging unit 1 obtains visible spectrum image data in a visible spectrum capture mode and obtains infra-red image data indicating a surface body temperature distribution for a subject's body in an infra-red capture mode. The regional temperature calculation unit 6 detects a temperature of an ocular center region within the surface body temperature distribution indicated by the infra-red image data. The weighted subtraction unit 7 applies a correction to a temperature parameter for drowsiness estimation, based on the detected ocular center region temperature. A drowsiness estimation for the user is then performed according to the corrected parameter.

11 Claims, 14 Drawing Sheets

(51) Int. Cl.
- *A61B 5/18* (2006.01)
- *B60K 28/06* (2006.01)
- *A61B 5/00* (2006.01)

(52) U.S. Cl.
CPC ............... *A61B 5/015* (2013.01); *A61B 5/18* (2013.01); *B60K 28/06* (2013.01); *G06K 9/0061* (2013.01); *G06K 9/00604* (2013.01)

(56) References Cited

U.S. PATENT DOCUMENTS

| | | | |
|---|---|---|---|
| 2004/0254472 A1* | 12/2004 | McQuilkin | A61B 5/015 600/473 |
| 2008/0180235 A1* | 7/2008 | Chang | A61B 5/01 340/449 |
| 2010/0289885 A1* | 11/2010 | Lu | H04N 5/2258 348/61 |

FOREIGN PATENT DOCUMENTS

| | | |
|---|---|---|
| JP | 2007-68620 | 3/2007 |
| JP | 2007-516018 | 6/2007 |
| JP | 2010-133692 | 6/2010 |

OTHER PUBLICATIONS

Y. Kamei et al., "Sleep Disorders—Modern Clinical Topics: Sleeping Soundly", Modern Physician, vol. 25, No. 1, pp. 55-59, Jan. 2005 and partial English translation.

Seika Aizawa et al., "Could the Ocular Surface Temperature be an Indication of Core Temperature?" Japan Society of Physical Anthropology, vol. 5, No. 1, pp. 31-38, Feb. 2000.

Toyo Yamazaki, "Continuous Monitoring of Deep Temperatures at Various Sites of the Body by the Deep Body Thermometer and Clinical Appraisals of the Method Part.1 Experimental Study", Journal of Tokyo Women's Medical University, vol. 51, No. 10, pp. 1441-1445, Oct. 1981.

* cited by examiner

FIG. 3A
Visible spectrum image
FIG. 3B
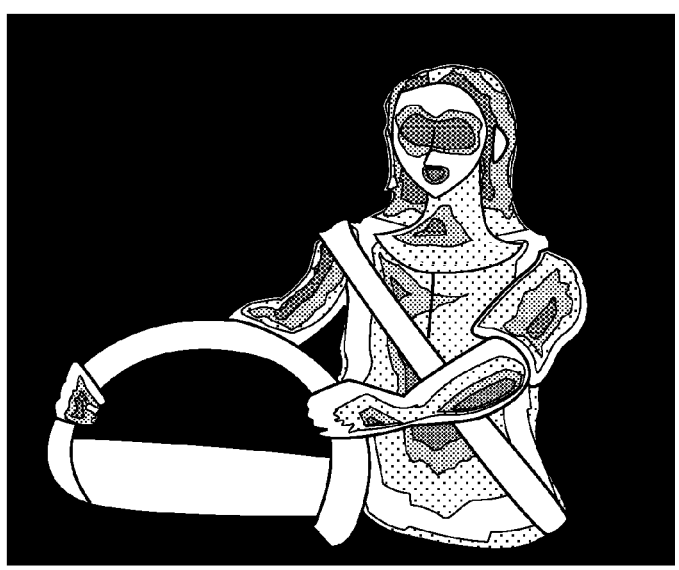
Infra-red image (surface body temperature distribution image)
FIG. 3C
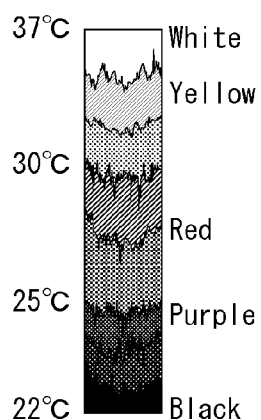
FIG. 3D
Image Data Pixel Values
| R luminance 0-255 | G luminance 0-255 | B luminance 0-255 | Transparency 0-255 |
|---|---|---|---|
| ← 8 bits → | ← 8 bits → | ← 8 bits → | ← 8 bits → |
| ← 32 bits → | | | |

FIG. 4A
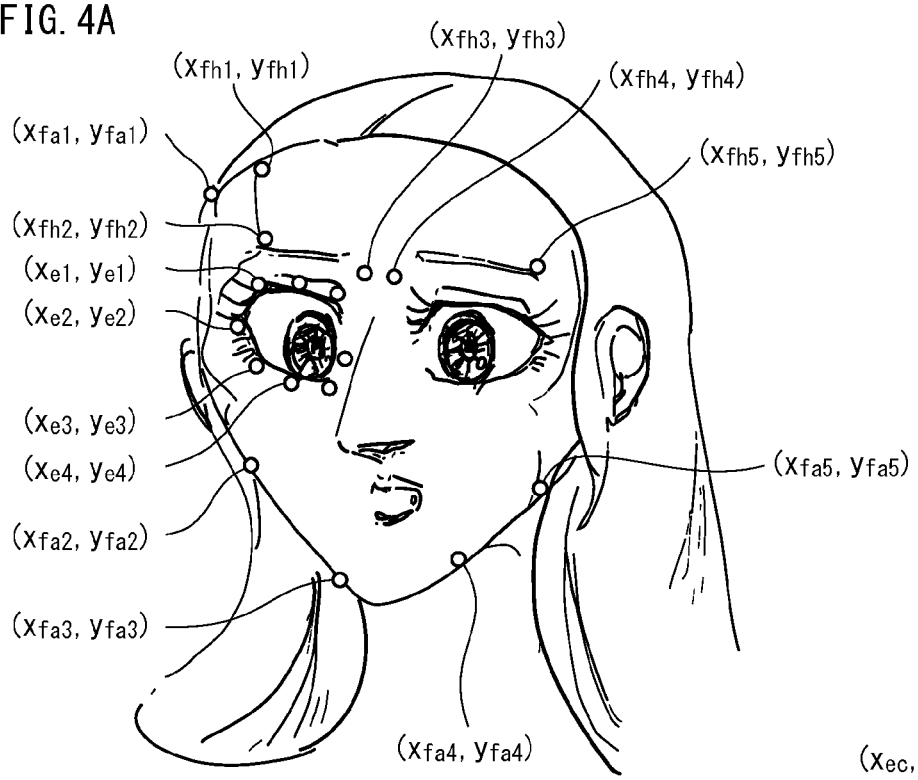
FIG. 4B
FIG. 4C
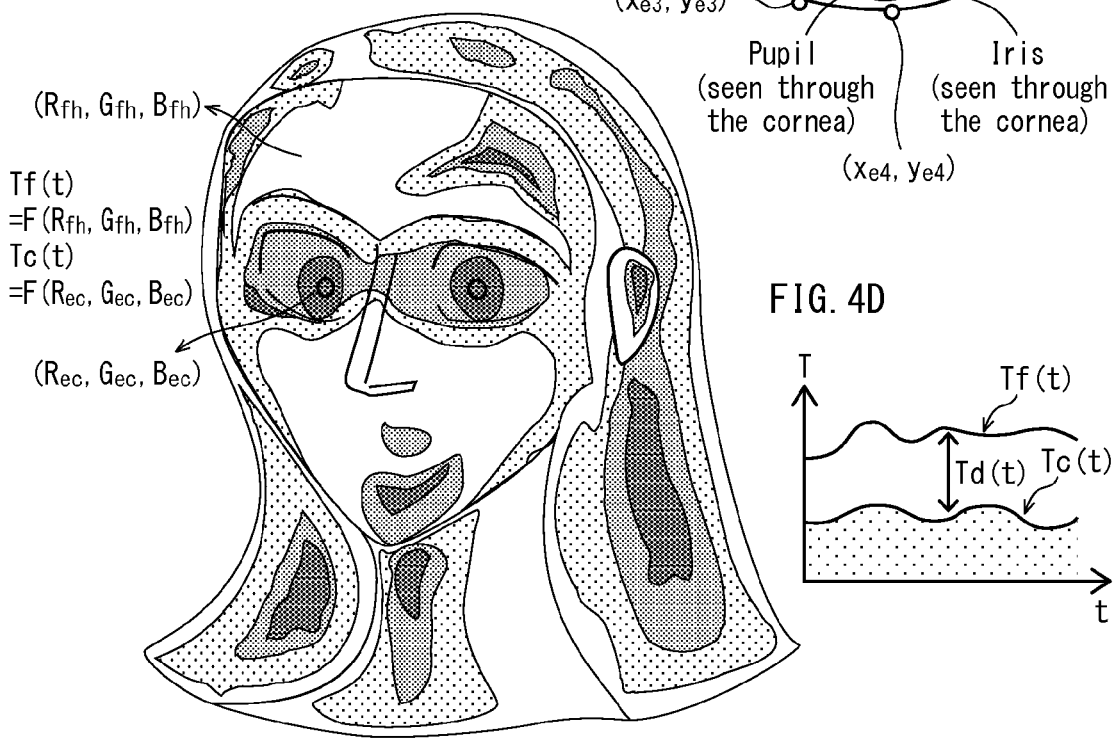
$Tf(t)$
$=F(R_{fh}, G_{fh}, B_{fh})$
$Tc(t)$
$=F(R_{ec}, G_{ec}, B_{ec})$
FIG. 4D
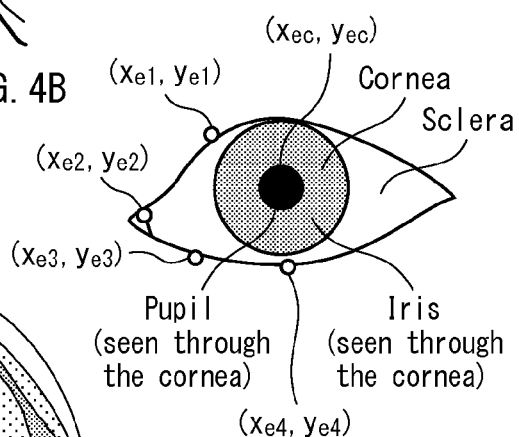

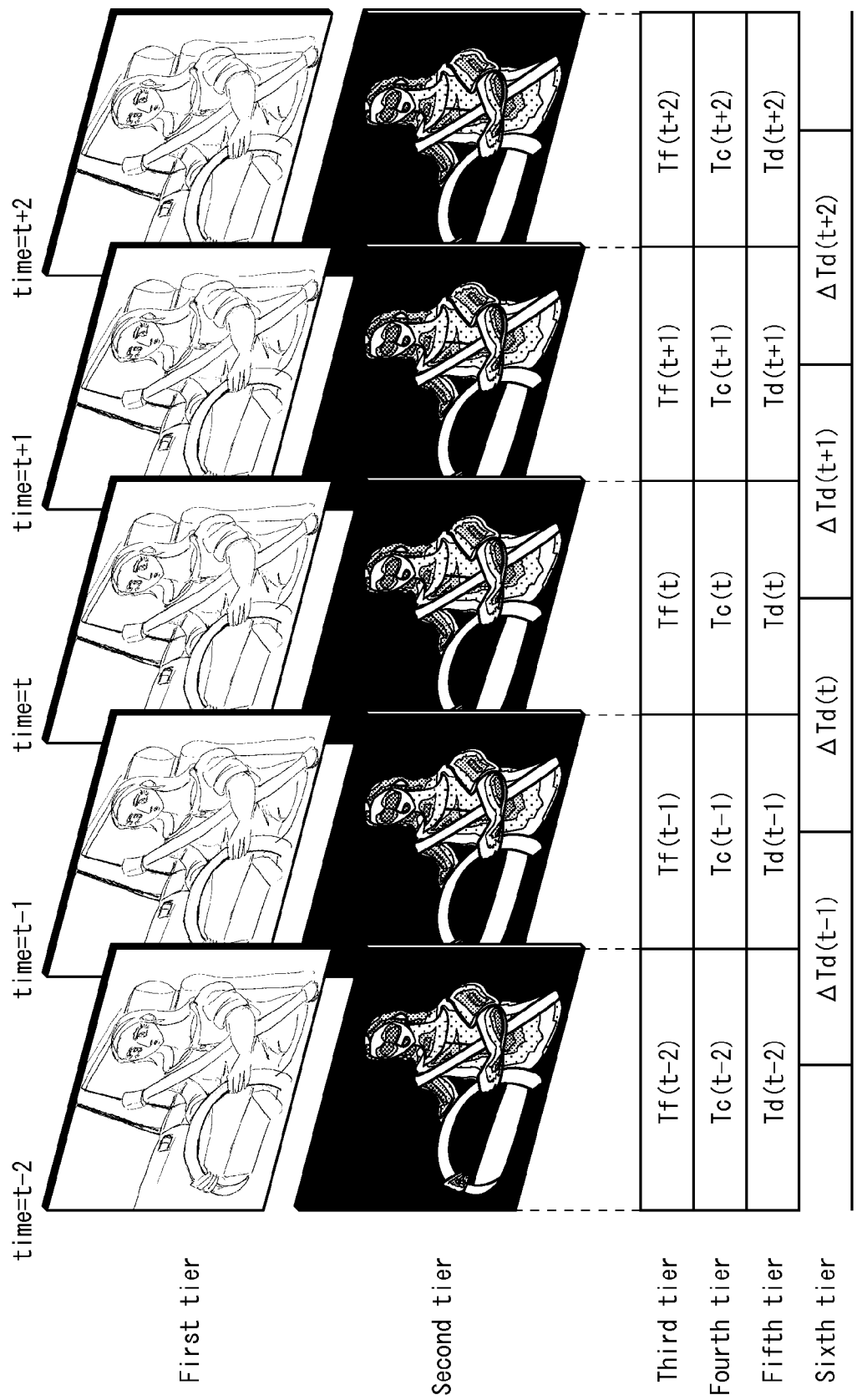

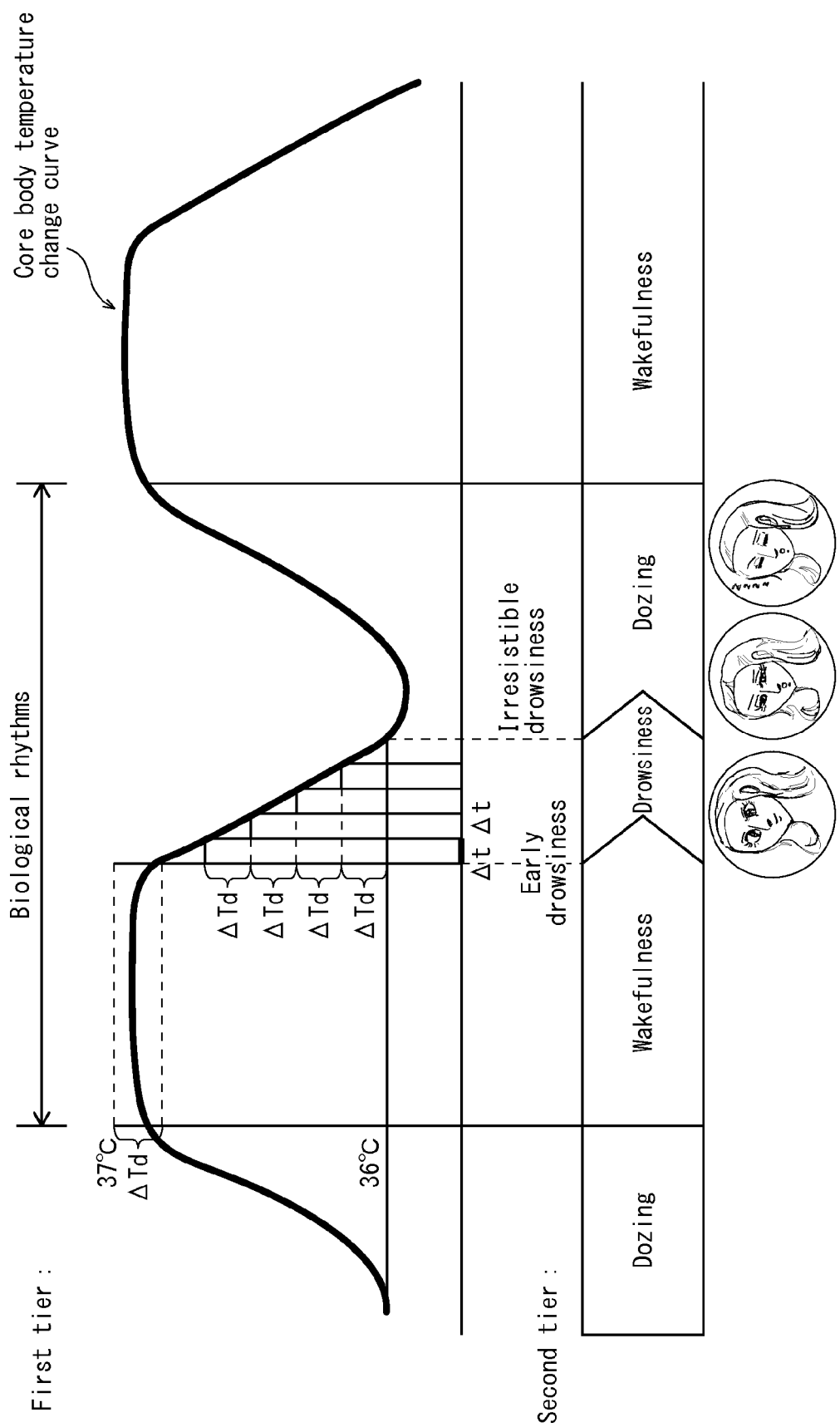

FIG. 13A
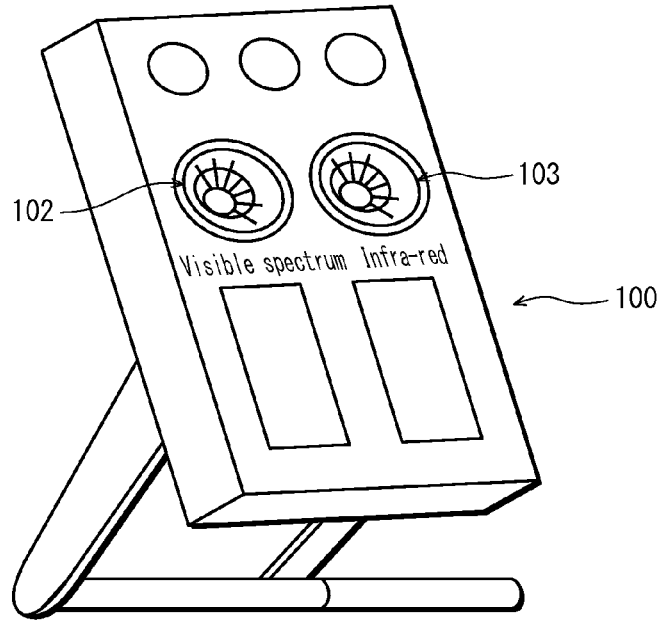
FIG. 13B
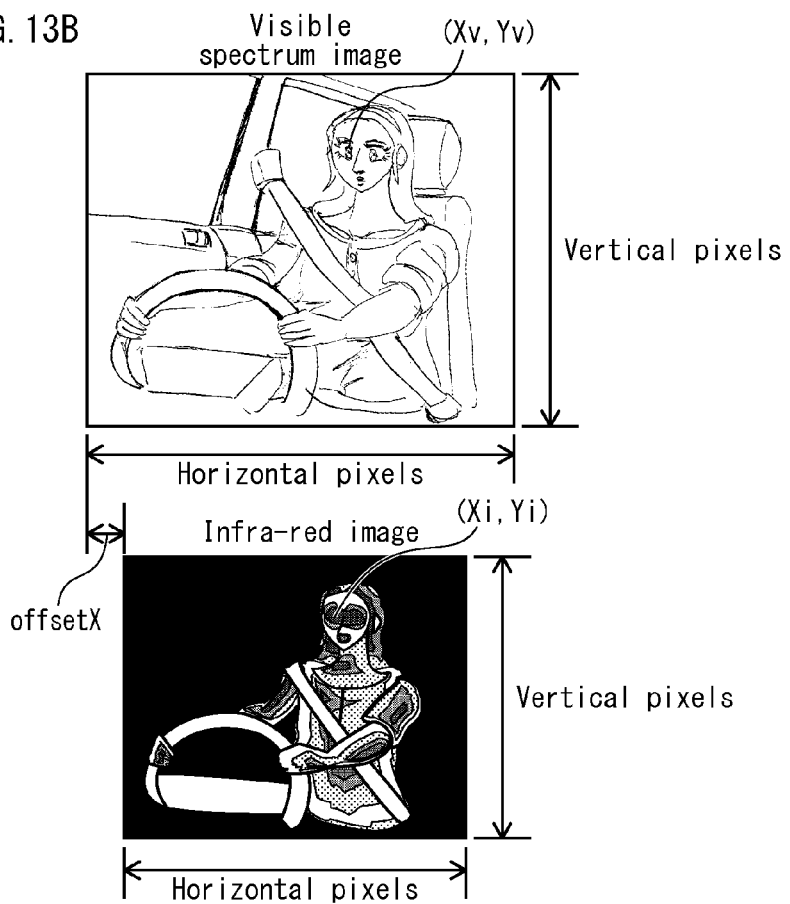
FIG. 13C
Xi=(infra-red image horizontal pixels/visible spectrum image horizontal pixels)×Xv+OffsetX
Yi=(infra-red image vertical pixels/visible spectrum image vertical pixels)×Yv FIG. 14A
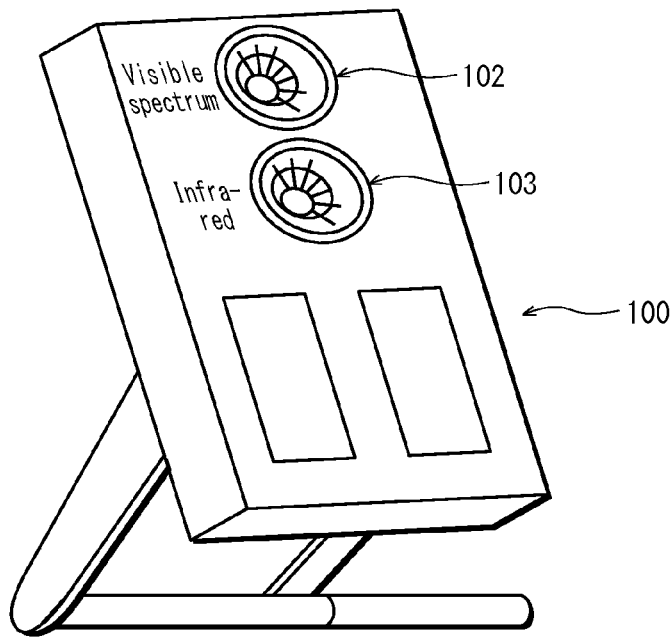
FIG. 14B
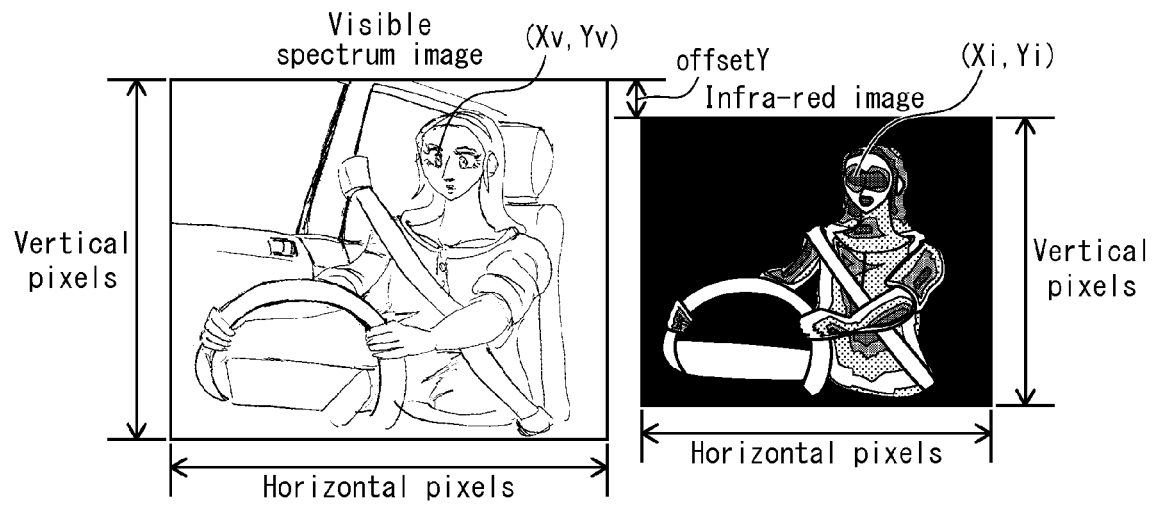
FIG. 14C
Xi=(infra-red image horizontal pixels/visible spectrum image horizontal pixels)×Xv
Yi=(infra-red image vertical pixels/visible spectrum image vertical pixels)×Yv+OffsetY

DROWSINESS ESTIMATION DEVICE, DROWSINESS ESTIMATION METHOD, AND COMPUTER-READABLE NON-TRANSIENT RECORDING MEDIUM

TECHNICAL FIELD

The present invention pertains to the technical field of analysing the biological rhythms of a user.

BACKGROUND ART

Technology for analysing the biological rhythms of a user involves performing analysis according to image data obtained by imaging the user, concerning whether or not a user is likely to succumb to drowsiness. In the field of medical instruments, technologies have long been used for this purpose. However, in recent years, the field of application has suddenly expanded, leading to realisation of applications in the automotive industry and in the home appliance industry. One application of biological rhythms analysis technology is a wakefulness detection device that detects wakefulness. Wakefulness detection involves detecting an eye region in an image obtained by imaging a user, and then detecting eyelid droop and a blink count to determine whether the user is in a wakefulness state or a dozing state.

CITATION LIST

Patent Literature

[Patent Literature 1]
Japanese Patent Application Publication No. H9-154835

Non-Patent Literature

[Non-Patent Literature 1]
Y. Kamei, S. Uchiyama, "Sleep Disorders—Modern Clinical Topics: Sleeping Soundly", Modern Physician Vol. 25 No. 1, pp. 55-59, January 2005

[Non-Patent Literature 2]
S. Aizawa, T. Nakajima, T. Nakanishi, J. Sugenoya, T. Ogawa, "Could the Ocular Surface Temperature be an Indication of Core Temperature?" Japanese Journal of Physiological Anthropology, Vol. 5, No. 1, pp. 31-38, February 2000

[Non-Patent Literature 3]
T. Yamazaki, "Continuous Monitoring of Deep Temperatures at Various Sites of the Body by the Deep Body Thermometer and Clinical Appraisals of the Method Part 2. Clinical Study" Journal of Tokyo Women's Medical University, Vol. 51, No. 10, pp. 1441-1445, October 1981

SUMMARY OF INVENTION

Technical Problem

Conventional wakefulness detection using imaging processing is a judgment regarding a dozing state, based on blink count and eyelid droop. However, dozing occurs when the user has succumbed to drowsiness. Detecting this state may be too late to be useful for applications such as accident prevention.

Accident prevention requires earlier detection using biological rhythms, that is, detecting a transition period between wakefulness and drowsiness. However, the transition period between wakefulness and drowsiness is difficult to perceive from changes in the blink count and eyelid droop. As such, the transition period between wakefulness and drowsiness is not detectable within the scope of the above-described image analysis.

Preventing accidents and avoiding decreased output by workers performing operations has long been a concern. Early detection, before the user enters a dozing state, is greatly expected to benefit various fields of business operation. However, no drowsiness estimation method currently exists that is capable of meeting these expectations.

The present disclosure aims to provide greater precision relative to conventional detection of a transition period between wakefulness and drowsiness.

Solution to Problem

In order to resolve the above-described problem, a drowsiness estimation device detecting a temperature parameter for a drowsiness estimation of a person subject to the drowsiness estimation, and performing the drowsiness estimation, the drowsiness estimation device comprising: an acquisition unit acquiring visible spectrum image data obtained by capturing a plurality of images of the person with visible spectrum wavelengths, and surface body temperature distribution data obtained by measuring a temperature distribution of a body surface of the person; an image processing unit specifying an ocular region centre for the person by performing image processing on the visible spectrum image data; and a correction unit detecting a temperature of the ocular region centre in the surface body temperature distribution data for the person, and using the temperature of the ocular region centre to apply a correction to the temperature parameter for the drowsiness estimation.

Advantageous Effects of Invention

The estimation unit uses a temperature parameter for drowsiness estimation concerning whether or not the user is approaching drowsiness. Furthermore, the temperature parameter is corrected according to an ocular centre region temperature, which sufficiently cancels out the effect of the surrounding environment on the temperature parameter. The change in temperature within the user's body during the transition period from wakefulness to drowsiness is reflected in the temperature parameter. Thus, the temperature parameter is usable for appropriately determining the state of drowsiness currently experienced by the user.

The determination of whether or not the user is approaching drowsiness may be made by extension from image processing performed on visible spectrum image data obtained by imaging the user. Thus, dozing monitoring is enabled using consumer devices typically handled by the user. Dozing monitoring may be introduced to various fields, making the extinction of sleep-related accidents a dream come true.

BRIEF DESCRIPTION OF DRAWINGS

FIGS. 3A and 3B respectively show visible spectrum image data and infra-red image data obtained by imaging a user at the wheel in a driver's seat, FIG. 3C indicates a relationship between pixel values in the infra-red image data and surface body temperature, and FIG. 3D indicates bit assignments for storing pixel data from the infra-red image data.

FIG. 4A shows detection results in a face region, an ocular region, and a forehead region, FIG. 4B indicates a magnification of the ocular region detected through ocular region detection, FIG. 4C illustrates portions of the infra-red image data subject to conversion, and FIG. 4D gives transitions in Tf(t) and Tc(t) over time.

FIG. 5 indicates the order in which Td is derived over time.

FIG. 6 indicates the relationship between biological rhythms and temperature.

FIG. 13A shows a perspective view of the drowsiness estimation device 100, FIG. 13B illustrates the visible spectrum image and the infra-red image, and FIG. 13C gives formulae for obtaining (Xi,Yi) from (Xv,Yv).

FIG. 14A shows a perspective view of the drowsiness estimation device 100, FIG. 14B illustrates the visible spectrum image and the infra-red image, and FIG. 14C gives formulae for obtaining (Xi,Yi) from (Xv,Yv).

DESCRIPTION OF EMBODIMENTS

Figure 1A:
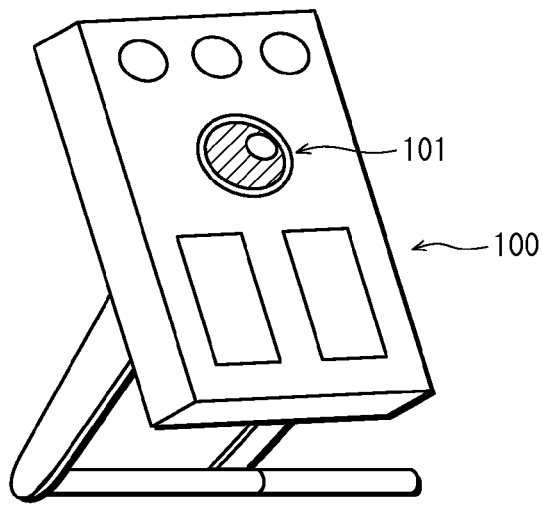
FIG. 1A shows a perspective view of a drowsiness estimation device 100.

The inventor addressed various technological difficulties in realising a device that resolves the above-described problems. The following describes the steps taken toward overcoming these technological difficulties.

According to Non-Patent Literature 1, the biological rhythms of drowsiness and wakefulness are created by an internal clock. The internal clock defines a set point for body temperature that maintains the biological rhythms of wakefulness and drowsiness. Heat production and heat dissipation mechanisms are used to adjust body heat produced and dissipated as the temperature approaches the set point. The internal clock is located in the suprachiasmatic nucleus. Thus, the core body temperature must be measured in order to obtain the set point that is used for biological rhythm maintenance. The core body temperature is the temperature of the heart, brain, and so on. The core body temperature is difficult to measure directly. Thus, an area is selected that is easy to measure and that approaches the core temperature.

Patent Literature 1 describes prior technology for detecting a transition period from wakefulness to drowsiness by measuring the body temperature in an area that is easy to measure and that approaches the core temperature. According to Patent Literature 1, temperature changes in the skin over the nose bone and masseter muscle, as well as air temperature changes, are detected at a given time and an average change is calculated for each. A moving average calculated therefor is then used to detect a decrease in wakefulness accompanied by changes in temperature of the skin over the nose, thus easily determining an early sign of dozing.

However, the technology of Patent Literature 1 requires that the effect of environmental temperature surrounding the user be taken into consideration when measuring the skin temperature. Thus, an air temperature sensor must be provided separately.

In addition, simple temperature detection is insufficient, as the effect of environmental temperature must be considered at a position closer to the place where skin temperature is detected. Typical room thermometers are ordinarily arranged far from a human body. Unavoidable error is produced by the distance between a room thermometer and a skin surface temperature detector. Further, the interior of a vehicle in operation is subject to dramatic differences in air temperature through the effects of direct sunlight, air conditioners, and so on. As such, detecting a change in temperature may not be sufficient for enabling a determination regarding whether the change is internal to the subject or related to the outside atmosphere. Thus, the prior technology described in Patent Literature 1 is not capable of performing a sufficiently precise determination regarding signs of dozing.

According to the above, the set point cannot be appropriately understood without cancelling out the effect of environmental temperature, regardless of where the sensor is worn on the user's body.

Embodiments for overcoming this challenge are presented below, with section 1 describing a basic aspect while sections 2, 3, and 4 describe further variants.

(1. Basic Aspect)

In one aspect, a drowsiness estimation device detecting a temperature parameter for a drowsiness estimation of a person subject to the drowsiness estimation, and performing the drowsiness estimation, the drowsiness estimation device comprising: an acquisition unit acquiring visible spectrum image data obtained by capturing a plurality of images of the person with visible spectrum wavelengths, and surface body temperature distribution data obtained by measuring a temperature distribution of a body surface of the person; an image processing unit specifying an ocular region centre for the person by performing image processing on the visible spectrum image data; and a correction unit detecting a temperature of the ocular region centre in the surface body temperature distribution data for the person, and using the temperature of the ocular region centre to apply a correction to the temperature parameter for the drowsiness estimation.

According to Non-Patent Literature 2, the temperature of an ocular centre region is an ocular surface temperature, and represents the temperature of the cornea where blood flow does not dominate. The ocular surface temperature may greatly vary along with environmental temperature changes, but such variation differs from variation in tympanic temperature, oesophageal temperature, average skin temperature, and forehead temperature. Parameter correction using the ocular centre region temperature is thus able to appropriately cancel out the influence of environmental temperature on the body.

(2. Ocular Centre Detection Details)

The ocular region centre detected in section 1 may be developed specifically as image content from the visible spectrum image. That is, in another aspect, the image processing unit specifies the ocular region centre by detecting an outline of a cornea in a face region of the person appearing in the visual spectrum image data, and specifying an arc centre as indicated by the outline of the cornea. The cornea outline forms an arc in the ocular region. This arc serves as a clue enabling comparatively easy specification of the ocular region centre.

(3. Drowsiness Estimation Parameter Acquisition Locations)

The location at which the core body temperature is acquired for the drowsiness estimation may be one of several, as specifically discussed below. The core body temperature is most accurately represented at the armpits, the oral cavity, the eardrum, and the rectum. However, attaching a sensor to the armpits, the oral cavity, the eardrum, or the rectum is not possible to non-medical operators and is not realisable for typical users. Also, attaching a sensor to the arms or legs causes a discrepancy in sensor precision, which damages product usability.

Thus, a contactless measurement method is desired that does not require attaching any sensors to the body. The drowsiness estimation by the contactless measurement method must be performed as follows.

That is, in a further aspect, the temperature parameter is a body temperature in a forehead region within a face region, and the correction unit obtains the temperature parameter by detecting a forehead region temperature from the surface body temperature distribution data.

According to Non-Patent Literature 3, the effect of environmental temperature must be cancelled out. Thus, the forehead is used to represent the core body temperature. The face region is detected and, upon detecting the ocular region, the forehead region temperature is acquired from a region located above the ocular region within the face region. Thus, the core body temperature is simply acquired, rather than requiring measurement of the armpits, the oral cavity, the eardrum, and the rectum. According to this configuration, the drowsiness estimation device is able to estimate drowsiness by detecting temperature changes, without using a sensor directly measuring temperature of the body. The lack of need to attack a sensor to the body is optimal for realisation.

(4. Locations to Exclude from Drowsiness Estimation Parameter Acquisition)

The location at which the parameter is acquired for the drowsiness estimation may be one of several, as specifically discussed below. That is, in an additional aspect, the temperature parameter is a body temperature of a portion of a face region, excluding a mouth region and a hairline region, and the correction unit obtains the temperature parameter by detecting a portion temperature in the face region excluding the mouth region and the hairline region, from the surface body temperature distribution data.

The areas surrounding the mouth and hairline are weakly related to core body temperature. Excluding these areas from core body temperature measurement is sufficient to correspondingly enhance core body temperature detection.

(5. Detailed Correction Using Core Body Temperature)

The following describes a specific approaching to using the drowsiness estimation parameter for correction. That is, in yet another aspect, the correction is applied to the temperature parameter by multiplying the temperature parameter and the temperature of the ocular region centre by respective first and second weighting coefficients, and subtracting a weighted temperature of the ocular region centre from a weighted temperature parameter. A weighting coefficient is applied to the temperature parameter and eye centre region temperature used for drowsiness estimation. This enables appropriate conversion of the temperature parameter and eye centre region temperature to be applied to drowsiness estimation. This conversion increases the precision of drowsiness estimation.

(6. Infra-Red Image Data Details)

The following specifically details a configuration pertaining the data used as surface body temperature distribution data. That is, in yet a further aspect, the surface body temperature distribution data are infra-red image data made up of a plurality of pixels and having a predetermined resolution, the pixels of the infra-red image data are in correspondence with pixels of the visible spectrum image data, and a colour component luminance of each of the pixels of the infra-red image data indicates an amount of infra-red radiation emitted by a corresponding portion of the body surface of the person appearing in the visual spectrum image data. Each pixel value in the infra-red image data indicates the amount of infra-red radiation at locations on the surface of the subject's skin. Thus, the core body temperature is calculable provided that the user appears in the infra-red image data. Accordingly, an appropriate pixel range for core body temperature is obtainable regardless of how the subject appears within the infra-red image data, which enables improvements to the detection precision for the core body temperature.

(7. Detection Region Coordinate Conversion)

Coordinate conversion may be introduced as a bridge for performing the ocular centre region detection and temperature conversion. That is, in still another aspect, the visual spectrum image data and the infra-red image data differ in resolution, the image processing unit specifies the ocular region centre using an X-coordinate or a Y-coordinate in a coordinate system of the visual spectrum image data, the correction unit applies a conversion to the X-coordinate or the Y-coordinate of the ocular region centre and converts a pixel value from the infra-red image data at a converted X-coordinate or a converted Y-coordinate into a temperature, and the conversion applied by the correction unit involves multiplying the X-coordinate or the Y-coordinate of the ocular region centre by a horizontal pixel ratio or a vertical pixel ratio of the visible spectrum image data and the infra-red image data, and then adding a horizontal offset or a vertical offset representing a cause of difference between a visible spectrum imaging system and an infra-red spectrum imaging system.

An error produced by the difference between the capture systems for respectively capturing the visible spectrum image and the infra-red and an error produced by the difference in resolution between the visible spectrum image and the infra-red are both absorbable. Thus, high cost-performance is achievable for the product equipped with the drowsiness estimation device.

(8. Drowsiness Estimation Details)

The following specifies a range defining the states in which drowsiness is felt. That is, in another additional aspect, the visible spectrum image data and the infra-red image data are obtained by capturing the images of the person at a plurality of imaging times in a measurement time slot, at each of the imaging times, the image processing unit specifies the ocular region centre, the acquisition unit acquires the infra-red image data, and the correction unit applies the correction to the temperature parameter, and the drowsiness estimation is performed by comparing a corrected temperature parameter for a given measurement time to a past corrected temperature parameter for a past measurement time, and determining whether a downward trend is occurring and whether a span of the downward trend exceeds a predetermined threshold.

The variation in core body temperature is represented as a model transition from wakefulness to drowsiness. Thus, an operation such as sounding an alarm can be performed while the user is only mildly drowsy. Also, the difference between the core body temperature obtained at each of a plurality of measurement times enables determination regarding the transition, and thus enables increased precision of drowsiness estimation.

(9. Addition to Imaging Unit)

An addition to the imaging unit may be provided as an optional component. That is, in another additional aspect, the drowsiness estimation device further includes an imaging unit that is switchable to one of a first mode of being transmissive to the visible spectrum wavelengths and opaque to infra-red wavelengths, and a second mode of being transmissive to the infra-red wavelengths and opaque to the visible spectrum wavelengths, wherein the visible spectrum image data and the infra-red image data are respectively obtained by switching between the first mode and the second mode.

A single imaging unit is able to obtain a visible spectrum image that uses visible spectrum wavelengths and infra-red image data that use infra-red wavelengths. This provides a tight correlation between pixel coordinates of the visible spectrum image and pixel coordinates of the infra-red image data. Thus, the temperature of each portion obtained by detecting the ocular region in the visible spectrum image data is derivable faithfully from the infra-red image data.

(10. Temperature Parameter Acquisition Variation)

Further variation may be applied to the temperature parameter acquisition. That is, in an alternative aspect, the temperature parameter for the drowsiness estimation is acquired by a contact sensor attached to an arm, a leg, and a collarbone of the person. The temperature parameter serving as a basis for drowsiness estimation is a measured value from a contact sensor having high reliability. Accordingly, the method described in Non-Patent Literature 3 is usable for core body temperature measurement, thus increasing the reliability of the core body temperature measurement.

(11. Overcoming Obstacles as Drowsiness Estimation Method)

In order to overcome obstacles to implementation as a method, the present disclosure provides a drowsiness estimation method used by a drowsiness estimation device detecting a temperature parameter for a drowsiness estimation of a person subject to the drowsiness estimation, and performing the drowsiness estimation, the drowsiness estimation method comprising: acquiring visible spectrum image data obtained by capturing a plurality of images of the person with visible spectrum wavelengths, and surface body temperature distribution data obtained by measuring a temperature distribution of a body surface of the person; performing image processing on the visible spectrum image data by specifying an ocular region centre for the person; and applying a correction to the temperature parameter for the drowsiness estimation by detecting a temperature of the ocular region centre in the surface body temperature distribution data for the person, and using the temperature of the ocular region centre to apply the correction. The method enables improvements to be applied to sections 2 through 10, described above. The drowsiness estimation method is usable by a corporate user, or in the location of the end user. This expands the applicability of the technology described herein.

(12. Overcoming Obstacles as a Computer Readable Recording Medium)

In order to overcome obstacles to implementation as a computer-readable recording medium, the present disclosure provides a computer-readable non-transitory recording medium on which one or more program codes are recorded for causing a computer to perform a drowsiness estimation of a person subject to the drowsiness estimation using a temperature parameter, by causing the computer to execute processing of: acquiring visible spectrum image data obtained by capturing a plurality of images of the person with visible spectrum wavelengths, and surface body temperature distribution data obtained by measuring a temperature distribution of a body surface of the person; performing image processing on the visible spectrum image data by specifying an ocular region centre for the person; and applying a correction to the temperature parameter for the drowsiness estimation by detecting a temperature of the ocular region centre in the surface body temperature distribution data for the person, and using the temperature of the ocular region centre to apply the correction. The recording medium enables improvements to be applied to sections 2 through 10, described above. This enables the program to be distributed through various recording media or a network provider server, thus expanding application to general computer software and online services.

The basic aspect of section 1, described above, and the variants of sections 2, 3, and 4, may be freely combined with two or more optional elements. Embodiments 1 through 5, described below, represent basic embodiments and variations thereof as models approaching a product version of the drowsiness estimation device. The Embodiments of the disclosure are described below with reference to the accompanying drawings.

Embodiment 1

Embodiment 1 pertains to the realisation of a drowsiness estimation device performing a drowsiness estimate by deriving an appropriate core temperature from a central temperature of an ocular region and a temperature of a forehead region. The drowsiness estimation device differs from the wakefulness detection device described as background art in detecting a transition period from wakefulness to drowsiness, and in using higher functionality than the wakefulness detection device. That is, the drowsiness estimation device is installed within a vehicle and performs biological rhythm monitoring of the driver using the device, and uses a number of user blinks or a degree of eyelid droop to determine whether the user is dozing, as well as to determine whether or not the user is in a transition period from drowsiness to wakefulness.

FIG. 1A shows a perspective view of a drowsiness estimation device 100. As shown, the drowsiness estimation device 100 includes a light reception unit for a camera 101. The camera 101 is both a visible spectrum and infra-red spectrum camera capable of capturing a visible light image and an infra-red image with a single imaging system.

Figure 1B:
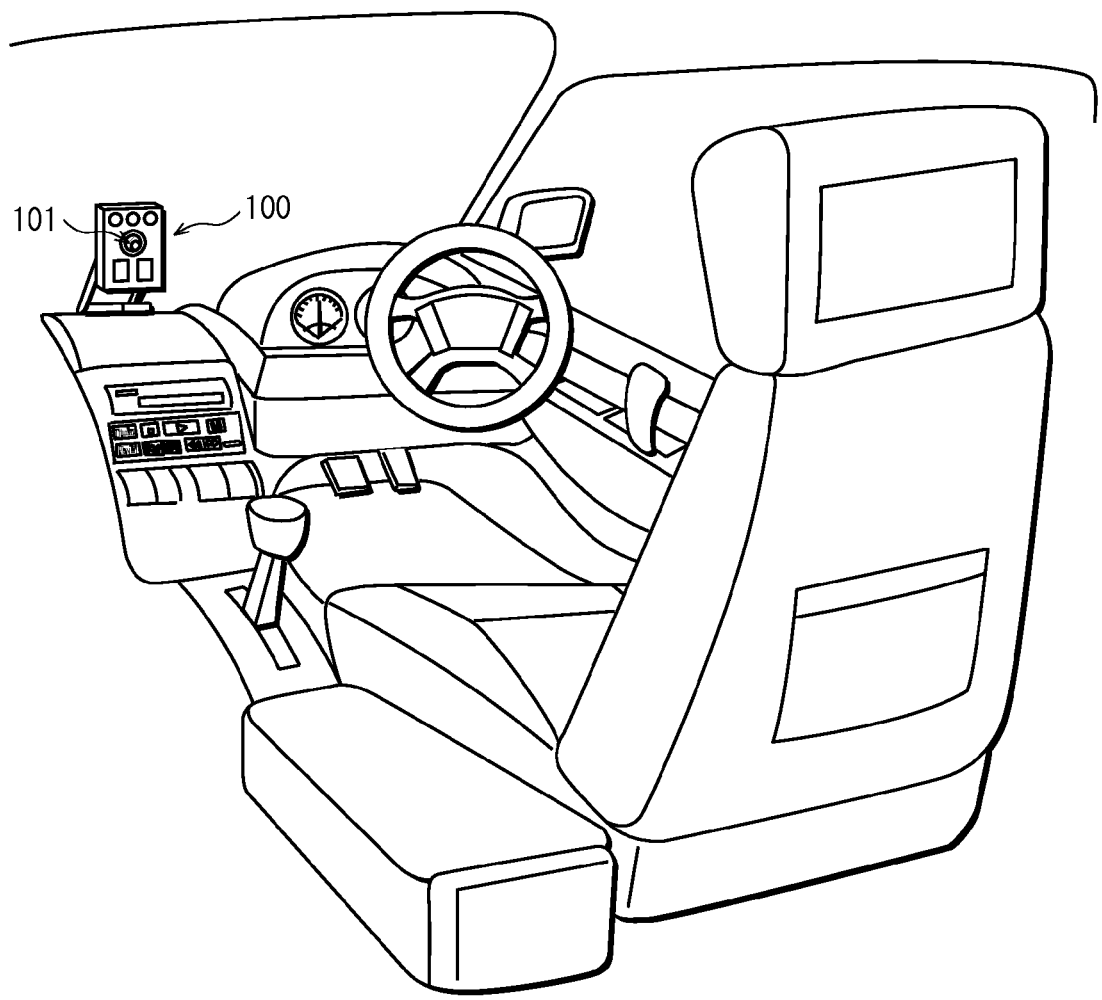
FIG. 1B illustrates an example of the drowsiness estimation device 100 as installed within a vehicle.

FIG. 1B illustrates an example of the drowsiness estimation device 100 as installed within a vehicle. When installed in a vehicle, the drowsiness estimation device 100 is mounted so as to face the user seated in the driver's seat.

Figure 2:
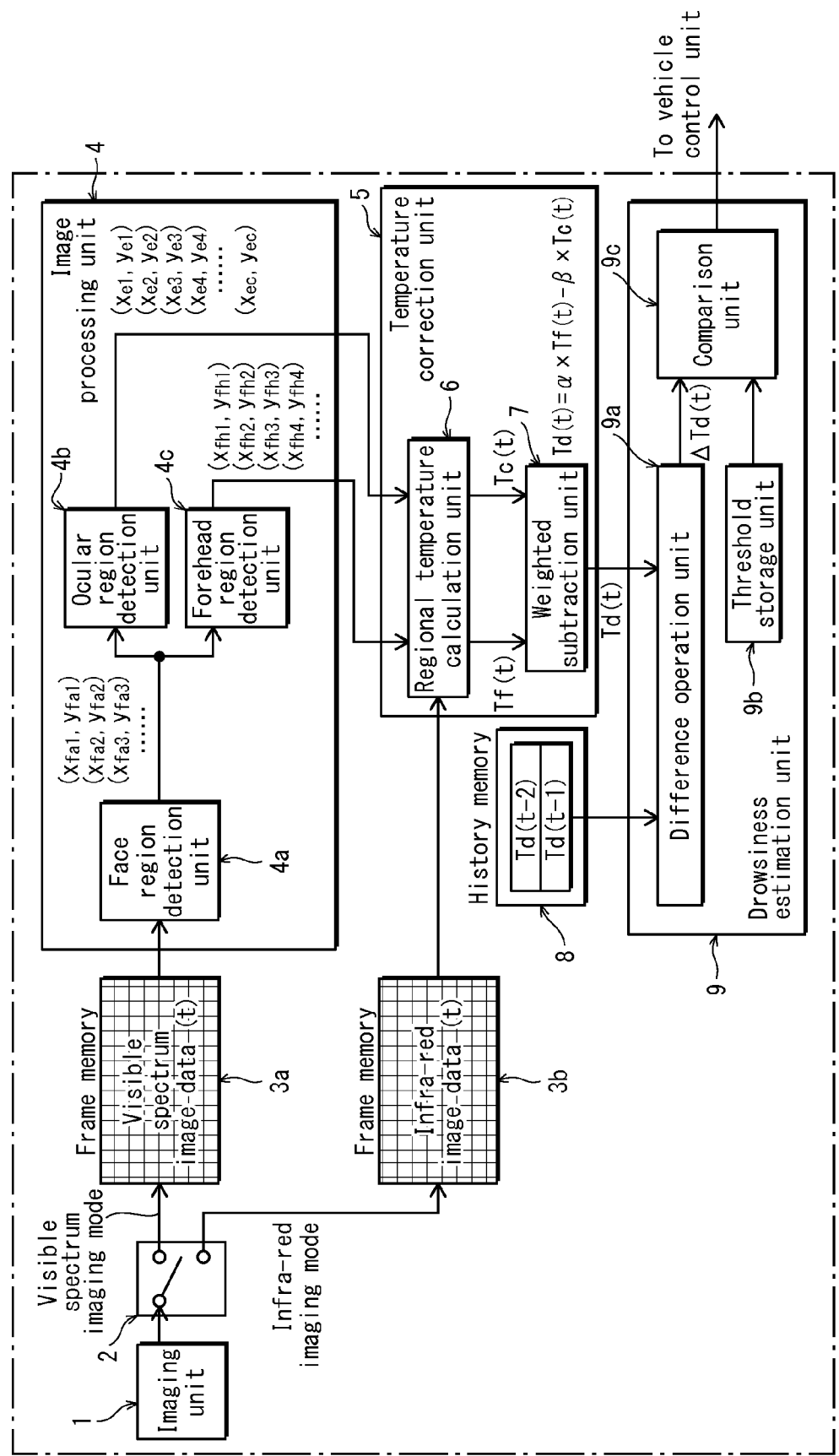
FIG. 2 shows the internal configuration of the drowsiness estimation device 100.

FIG. 2 shows the configuration of the drowsiness estimation device 100. As shown, the drowsiness estimation device 100 includes an imaging unit 1, a switching unit 2, frame memory 3a and 3b, an image processing unit 4, a temperature correction unit 5, a regional temperature calculation unit 6, a weighted subtraction unit 7, a history memory 8, and a drowsiness estimation unit 9.

The imaging unit 1 uses a common visible-infrared spectrum camera 101 to capture a image in visible spectrum wavelengths and an image in infra-red wavelengths at predetermined intervals, and outputs image data for one captured screen. The imaging unit 1 includes an imaging element that uses a photoelectric conversion element such as a CCD sensor or a CMOS sensor. In an infra-red capture mode, values for each pixel output from the imaging element serve as temperature information of a position corresponding to each pixel. The imaging unit 1 creates a temperature distribution for the image by arranging the temperature information corresponding to each pixel in the plane of the frame memory 3b, thereby obtaining infra-red spectrum data.

The switching unit 2 stores a mode setting indicating whether the device is currently in a visible spectrum capture mode or in an infra-red capture mode, and switches the destination of the image data obtained by the imaging unit 1 from frame memory 3a to frame memory 3b or from frame memory 3b to frame memory 3a in accordance with the mode setting.

Frame memory 3a stores a screen of pixel data transferred from the imaging unit 1 as visible spectrum data. The visible spectrum data stored in frame memory 3a are used for face region detection and eye detection.

Frame memory 3b sores a screen of pixel data transferred from the imaging unit 1 in the infra-red capture mode as infra-red spectrum image data. In contrast to the visible spectrum image data used for face and eye detection, the infra-red spectrum image data are used for temperature calculation. Detailed subject features appear in the visible spectrum image data for use in the face and eye detection, while such details are not necessary in the infra-red spectrum image data.

The image processing unit 4 is configured as a signal processing circuit that includes a digital signal processor and so on. The image processing unit 4 performs region detection on the visible spectrum image stored in the frame memory 3a and obtains a sequence of coordinate groups each indicating a desired region within the visible spectrum image data. The image processing unit 4 includes a face region detection unit 4a detecting a face region, an ocular region detection unit 4b detecting an ocular region, and a forehead region detection unit 4c detecting a forehead region. Coordinates $(x_{fa1}, y_{fa1})$, $(x_{fa2}, y_{fa2})$, $(x_{fa3}, y_{fa3})$ and so on in FIG. 2 are obtained from the detection performed by the face region detection unit 4a. Similarly, coordinates $(x_{e1}, y_{e1})$, $(x_{e2}, y_{e2})$, $(x_{e3}, y_{e3})$, $(x_{e4}, y_{e4})$ and so on are obtained by the ocular region detection unit 4b. These coordinates serve as a basis for a determinations pertaining to a blink count and to eyelid droop as part of dozing detection. Likewise, coordinates $(x_{fh1}, y_{fh1})$, $(x_{fh2}, y_{fh2})$, $(x_{fh3}, y_{fh3})$, $(x_{fh4}, y_{fh4})$ and so on are obtained by the forehead region detection unit 4c. Coordinates $(x_{ec}, x_{ec})$ in FIG. 2 indicate the centre of the cornea, which is the centre of the ocular region. The ocular region detection unit 4b detects the ocular region as well as an arc within the ocular region, and obtains coordinates for the centre of a circular region of which the arc forms a part. The circular region is the cornea. With respect to the visible spectrum image data, the cornea is partially hidden by the eyelid. The ocular region detection unit 4b detects an outline of the circular region and derives coordinates for the centre of the circular region therefrom.

The temperature correction unit 5 obtains a core body temperature by correcting drowsiness estimation parameters using a temperature at a position on the body appearing in the infra-red spectrum data indicated by specific coordinates.

The regional temperature calculation unit 6 is a component of the temperature correction unit 5 receiving a coordinate group specifying a given position in the visible spectrum image data from the image processing unit 4 and converting pixel values of pixels in the infra-red image data at the position specified by the coordinate group into a temperature. The temperature conversion involves converting pixel values into temperatures, for pixels at coordinates acquired for the infra-red spectrum data from the image processing unit 4. The imaging unit 1 obtains the infra-red image data by converting infra-red radiation amounts from the infra-red capture mode into pixel values. The regional temperature calculation unit 6 has a look-up table indicating a correspondence relationship for conversion between infra-red radiation amounts and pixel values. The look-up table is used to acquire a surface body temperature for the user, based on pixel values in the infra-red image data. The coordinates output by the image processing unit 4 define the ocular region and the forehead region. Thus, temperatures of the ocular region and forehead region are obtained through this conversion by the regional temperature calculation unit 6.

The weighted subtraction unit 7 is a component of the temperature correction unit 6. For a given measurement time t, the weighted subtraction unit 7 obtains a core body temperature Td(t) for measurement time t by applying coefficient α to the forehead region temperature Tf(t) obtained from the infra-red image data, and subtracting an ocular region temperature Tc(t) to which coefficient β has been applied.

A conversion formula for computing Td(t) by correcting Tf(t) using Tc(t) is given below. Here, α is a forehead temperature coefficient and β is a cornea temperature coefficient.

$$Td(t) = \alpha \times Tf(t) - \beta \times Tc(t) \quad \text{[Math 1]}$$

The history memory 8 stores a list of past core body temperatures in association with corresponding measurement times.

The drowsiness estimation unit 9 determines whether or not the user is in a transition period from wakefulness to drowsiness according to a change in core body temperature Td(t) over a plurality of times. The drowsiness estimation unit 9 includes a difference operation unit 9a subtracting a previous core body temperature Td(t−1) from the core body temperature Td(t) at measurement time t to obtain a change ΔTd, a threshold storage unit 9b storing a threshold for determination regarding the transition period from wakefulness to drowsiness, and a comparison unit 9c comparing the change ΔTd(t) to the threshold. According to this configuration, drowsiness is detected when the temperature of the forehead region is decreasing and the range of decrease exceeds a predetermined threshold. A drowsiness estimation result is then output. The drowsiness estimation uses a plurality of core body temperatures each measured at a different past measurement time. However, using a plurality of core body temperatures for the drowsiness estimation complicates the explanations that follow. As such, the past core body temperatures used for drowsiness estimation are simplified to the previous estimated value Td(t−1), below.

The following describes the components of the drowsiness estimation device 100. The principles of drowsiness estimation by the drowsiness estimation device 100 are discussed below. The following explanations are given with reference to FIGS. 3A-3D, 4A-4D, 5, and 6. The drowsiness estimation device 100 is mounted on a front panel of an automobile, as shown in FIG. 1B. When the drowsiness estimation device 100 is activated while mounted in this way, the imaging unit 1 captures images of the user sitting in the driver's seat in the visible spectrum capture mode and in the infra-red capture mode. The imaging unit 1 performs imaging. The switching unit 2 switches the destination of the visible spectrum image data and the infra-red image data to frame memory 3a and frame memory 3b as appropriate according to the mode setting, such that frame memory 3a receives the visible spectrum image data of FIG. 3A and frame memory 3B receives the infra-red image data. FIGS. 3A and 3B are associated images respectively representing the visible spectrum image data captured by the imaging unit in the visible spectrum capture mode and the infra-red image data captured by the imaging unit in the infra-red capture mode. FIG. 3A represents a user in the driver's seat holding the steering wheel. FIG. 3B represents infra-red image data. Typically, the resolution of infra-red image data is lower than the resolution of visible spectrum image data. As such, a plurality of pixels in the visible spectrum image data correspond to one pixel of distribution image data, while the infra-red image data represents infra-red radiation from the surface of the body of the user appearing in the visible spectrum image data. In the image data, portions having the same colour are producing the same amount of infra-red radiation. In FIG. 3B, portions corresponding to the user's skin are coloured within a range of average human body temperatures.

FIG. 3C is a graph indicating the relationship between the pixel values in the infra-red image data and surface temperature. The colour of the pixels in the infra-red image data varies according to the amount of infra-red radiation from the corresponding part of the user's body, e.g., progressing through black, purple, red, yellow, and white. A change from black to purple indicates a change from 22° C. to 25° C., and a change from red to white indicates a change from 27° C. to 37° C., for example.

The infra-red image data includes pixel values representing temperature changes as a combination of a red component, a green component, and blue component (i.e., RGB values), or as a combination of luminance, red-difference, and blue-difference (i.e., YCrCb values). The following describes a storage method for storing the pixel values of the infra-red image data in storage elements of frame memory 3b (Although the pixel values may be represented as RGB values or as YCrCb values, only RGB values are used in the following explanation for the sake of simplicity).

Each storage element of frame memory 3b has a 32-bit word length. FIG. 3D shows bit assignments for storing the pixel value data from the infra-red image data in frame memory 3b. Each pixel has 32 bits of data organised into four 8-bit segments from the highest-order bit to the lowest-order bit, each segment respectively representing a red component luminance (R), a green component luminance (G), a blue component luminance (B), and a transparency as a numerical value ranging from 0 to 255. The transparency of the infra-red image pixel data is used for making adjustments when displaying the infra-red image with a background GUI or a desktop image. The visible spectrum image data and the infra-red image data are subject to detection by the face region detection unit 4a, the ocular region detection unit 4b, and the forehead region detection unit 4c of the image processing unit 4. The coordinates indicated in FIG. 4A are detected in the visible spectrum image data by having the face region detection unit 4a, the ocular region detection unit 4b, and the forehead region detection unit 4c respectively perform face region detection, ocular region detection, and forehead region detection.

FIG. 4A shows detection results from the drowsiness estimation unit 9. Coordinates $(x_{fa1}, y_{fa1})$, $(x_{fa2}, y_{fa2})$, $(x_{fa3}, y_{fa3})$, $(x_{fa4}, y_{fa4})$ and so on in FIG. 4A specify an outline of the face. Similarly, coordinates $(x_{e1}, y_{e1})$, $(x_{e2}, y_{e2})$, $(x_{e3}, y_{e3})$, $(x_{e4}, y_{e4})$ and so on specify an outline of the ocular region, and coordinates $(x_{fh1}, y_{fh1})$, $(x_{fh2}, y_{fh2})$, $(x_{fh3}, y_{fh3})$, $(x_{fh4}, y_{fh4})$ and so on specify an outline of the forehead. FIG. 4B indicates a magnification of the ocular region detected through ocular region detection. Coordinates $(x_{ec}, x_{ec})$ in FIG. 4B indicate the centre of the cornea, which is the centre of the ocular region. When the visible spectrum image data are captured at high resolution, such as a 1K image (1920× 1080) or a 4K image (7680×4320), the results of detection by the face region detection unit 4a, the ocular region detection unit 4b, and the forehead region detection unit 4c reproduce the shapes of the user's face, eyes, and forehead, as well as the coordinates of the ocular region centre, with greater precision. These coordinates are transmitted to the regional temperature calculation unit 6. Among the pixel values of the infra-red image data, the regional temperature calculation unit 6 performs conversion into temperature on pixel values at the centre of the ocular region as output by the ocular region detection unit 4b and pixel values at an area surrounded by a coordinate group output by the forehead region detection unit 4c. FIG. 4C indicates the positions of portions subject to this conversion, within the infra-red image data.

FIG. 4C indicates the temperatures of each portion infra-red image data as calculated. In FIG. 4C, $(R_{ec}, G_{ec}, B_{ec})$ represents pixel values (i.e., RGB values in the present Embodiment) for a pixel at coordinates $(x_{ec}, y_{ec})$ in the infra-red image data. Coordinates $(x_{ec}, y_{ec})$ represent the ocular region centre. Thus, the RGB values of those coordinates are converted into temperature to calculate the ocular region temperature Tc.

Also, $(R_{fh}, G_{fh}, B_{fh})$ represents an average RGB value of the pixels at positions surrounded by coordinates $(x_{fh1}, y_{fh1})$, $(x_{fh2}, y_{fh2})$, $(x_{fh3}, y_{fh3})$, $(x_{fh4}, y_{fh4})$ and so on. The formulae printed to the left of FIG. 4C reading $Tf(t)=F(R_{fh}, G_{fh}, B_{fh})$ and $Tc(t)=F(R_{ec}, B_{ec}, G_{ec})$ are conversion formulae for deriving Tf from $(R_{fh}, G_{fh}, B_{fh})$ and Tc from $(R_{ec}, G_{ec}, B_{ec})$. The forehead temperature Tf and the ocular region centre temperature Tc are not fixed, but vary over time. FIG. 4D indicates Tf(t) and Tc(t) varying over time. In the coordinate system of FIG. 4D, the horizontal axis represents time while the vertical axis represents temperature. Thus, variation curves for Tf(t) and Tc(t) are drawn with respect to this coordinate system. Here, Td(t) indicates the difference between Tf(t) and Tc(t) at a given x-coordinate along the chronological axis of the coordinate system.

As the capturing by the imaging unit 1 continues in the visible spectrum capture mode and the infra-red capture mode, the above-described region detection and temperature conversion are repeatedly performed. FIG. 5 indicates the results of repeatedly performing the above-described region detection and temperature conversion over a period including the five times t−2, t−1, t, t+1, and t+2.

FIG. 5 indicates the order in which Td is derived over time. The first tier shows the visible spectrum image data measured at measurement times t−2, t−1, t, t+1, and t+2. The second tier shows the infra-red image data measured at measurement times t−2, t−1, t, t+1, and t+2. The third tier indicates the forehead region temperatures (Tf(t−2), Tf(t−1), Tf(t), Tf(t+1), Tf(t+2)) obtained from the infra-red image data imaged at each time, and the fourth tier indicates the ocular region temperatures (Tc(t−2), Tc(t−1), Tc(t), Tc(t+1), Tc(t+2)) similarly obtained from the infra-red image data at each time. The weighted subtraction unit 7 performs the weighted subtraction on the forehead temperature Tf(t) and the ocular centre temperature Tc(t) for each measurement time t−2, t−1, t, t+1, and t+2 to calculate the corresponding core body temperatures Td(t). Furthermore, as long as the core body temperature Td(t) is calculated at each measurement time, the drowsiness estimation unit 9 calculates the difference relative to the previous core body temperature Td(t−1). Accordingly, the difference ΔTd between the core body temperature Td at each measurement time is obtained. The current state of the user is detected as being one of wakefulness, drowsiness, and dozing, according to biological rhythms and using the direction of the change ΔTd.

The fifth tier indicates values of Td(t−2), Td(t−1), Td(t), Td(t+1), Td(t+2) obtained from Tc and Tf as calculated from the visible spectrum image at each time. The sixth tier indicates the core body temperature difference ΔTd(t−1), ΔTd(t), ΔTd(t+1) between measurement times.

FIG. 6 indicates the relationship between biological rhythms and temperature. The second tier indicates the biological rhythms repeatedly cycling between wakefulness, drowsiness, and dozing. The first tier indicates a variation curve for Td. The curve indicates the change in Td over time, in correspondence with wakefulness, drowsiness, and dozing. As shown, Td is mostly stable during wakefulness, such that the variation in Td between measurement times approaches zero. Upon transition from wakefulness to drowsiness, Td curves downward. During this transition from wakefulness to drowsiness, the difference ΔTd trends downward over a wide range. The core body temperature change ΔTd being negative and widely ranging is indicative of the transition period from wakefulness to drowsiness. These traits do not appear during states of wakefulness and drowsiness. Thus, identifying the traits of the core body temperature difference ΔTd as being negative and having an absolute value that is greater than a predetermined threshold enables a correct determination to the effect that the user is in a transition period from wakefulness to drowsiness. In FIG. 6, determination results indicating dozing are returned when the change ΔTd has a narrow range. Given that ΔTd indicates a sign of drowsiness, actions such as issuing a warning or making an outside notification may be performed as the user enters the state of drowsiness.

The bottom the second tier of FIG. 6 shows a changing facial expression of the user. The user's facial expression does not change when entering the transition period from wakefulness to drowsiness. However, during a transition period from drowsiness to dozing, the eyelids droop greatly and become completely closed upon dozing. The drowsiness estimation device 100 is able to detect the tinge of drowsiness in the early stages, while the user's facial expression is no different than during wakefulness.

When the user experiences a sudden attack of sleepiness, the corresponding droop suddenly increases in magnitude. This, combined with a sudden drop in core body temperature, serves as a clue for detecting the transition from wakefulness to drowsiness and enables early warning of danger signs. This concludes the explanation of drowsiness estimation principles for the drowsiness estimation device 100.

Figure 7:
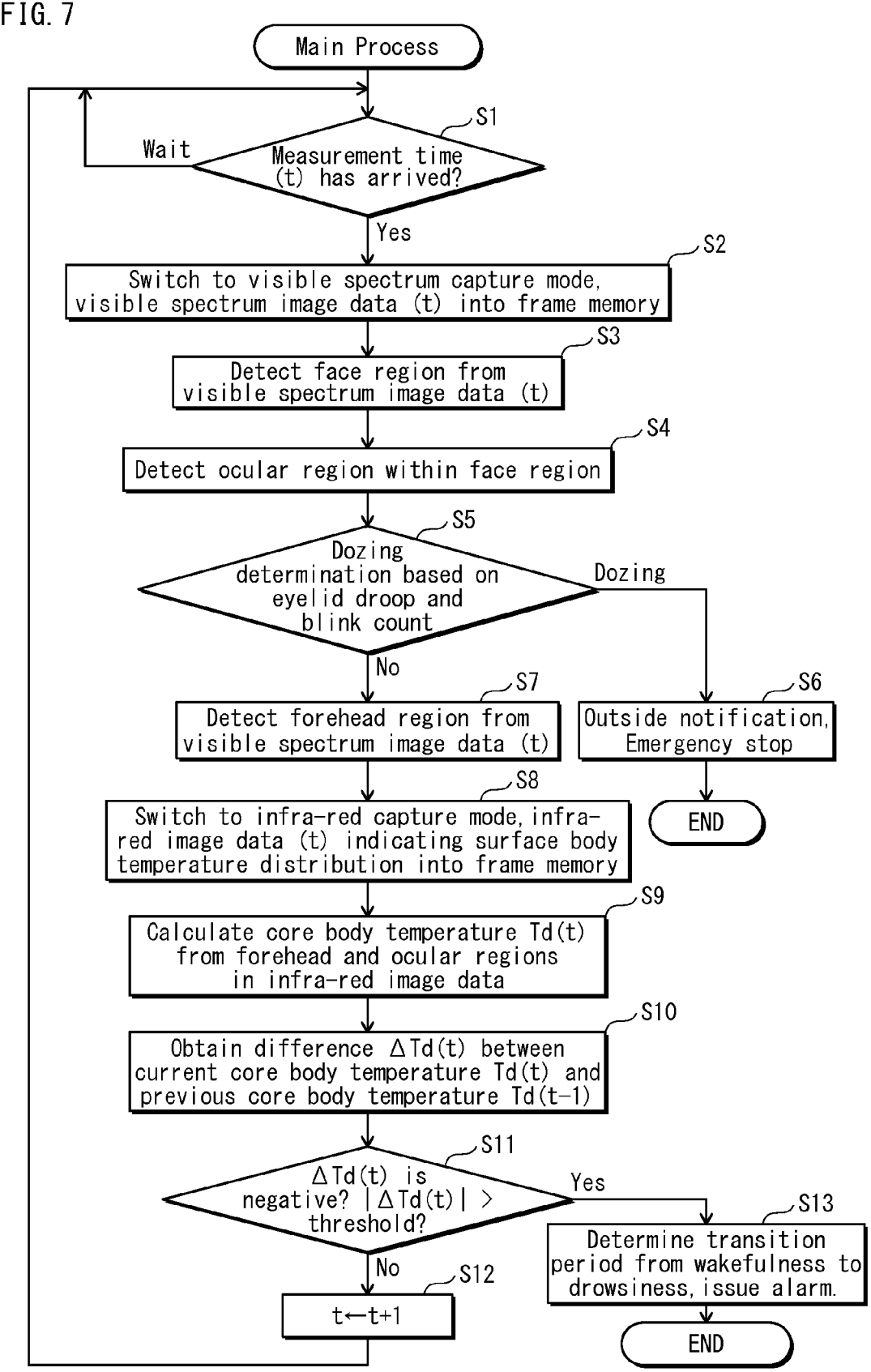
FIG. 7 is a flowchart of a main routine for drowsiness estimation device operations.
Figure 8:
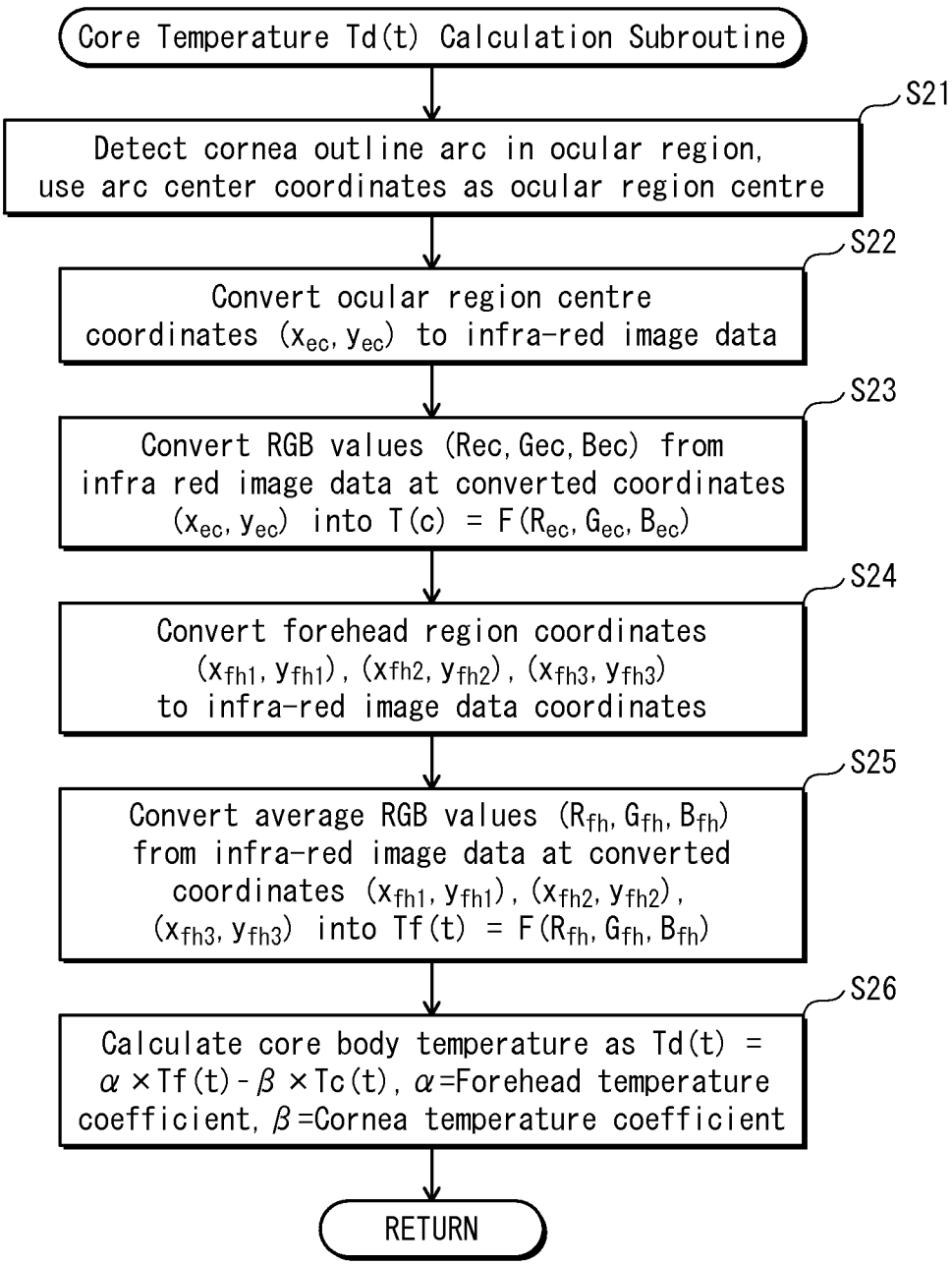
FIG. 8 is a flowchart of a subroutine for core body temperature operations.

The processing by the components of the drowsiness estimation device 100 described thus far is generalizable to a process for hardware resources in response to various external phenomena and internal device parameters. FIGS. 7 and 8 are flowcharts representing such generalised processing. Variables listed in the flowcharts indicate variables subject to processing among a plurality of information elements within the data structure. Also, the variable (t) in the flowcharts is a control variable for specifying an information element subject to processing. Accordingly, the following flowcharts specify visible spectrum image data (t) as being visible spectrum image data imaged at measurement time t, and infra-red image data (t) as infra-red image data imaged at measurement time t. Similarly, ocular region temperature Tc(t), forehead region temperature Tf(t), and core body temperature Td(t) are each calculated for measurement time t.

The flowchart of FIG. 7 is for highest-order processing, i.e., for a main routine. The flowchart of FIG. 8 is for a lower-order routine. The following describes the processing of the main routine.

Steps S1 through S12 are performed as a repeating loop. The end conditions for the loop are a determination result of Yes in step S5 or in step S11. Steps S2 through S11 are repeated until one of these conditions is satisfied. The control variable is incremented for each iteration of the loop. As such, the variable indicated by the visible spectrum image data and the infra-red image data is associated with the loop processing.

Step S1 is a determination regarding whether or not measurement time (t) has arrived. Upon reaching measurement time (t), the process of steps S2 through S5 is performed. This process involves switching the optical system to the visible spectrum capture mode and obtaining visible spectrum image data in the frame memory (step S2), detecting the face region in the visible spectrum image data (t) (step S3), and detecting the ocular region within the face region (step S4). Then, in step S5, a dozing determination is performed by reference to a quantity of blinks or a degree of eyelid droop in the ocular region. When dozing is detected, the process exits the loop and proceeds to an external warning, emergency stop, or similar measure. The present flowchart ends there.

When dozing is not detected, the process continues as follows. The forehead region is detected in the visible spectrum image data (t) (step S7). Then, the imaging unit 1 is switched to the infra-red capture mode and infra-red image data is acquired for the frame memory (step S8). The forehead region and ocular region in the infra-red image data are used to calculate Td(t) (step S9). The difference ΔTd(t) is calculated using the core body temperature Td(t) from the current loop and the previous core body temperature Td(t−1) (step S10). When ΔTd(t) is negative, a determination is made regarding whether or not the absolute value of ΔTd(t) is greater than a predetermined threshold (step S11). In the negative case, the measurement time t is incremented in step S12 and the process returns to step S1. In the affirmative case, the process exits the loop and proceeds to step S13, where a determination is made such that the user has entered the transition period from wakefulness to drowsiness, and an alarm is activated FIG. 8 indicates the core body temperature calculation process. The process described by this flowchart is a subroutine representing details of step S9 from FIG. 7.

First, an arc of a circle that is the outline of the cornea is detected in the ocular region, and the centre of the arc is used as the coordinates $(x_{ec}, y_{ec})$ of the ocular region centre (step S21). The ocular region centre coordinates $(x_{ec}, y_{ec})$ are converted into the coordinate system of the infra-red image data (step S22). Then, the conversion $Tc(t)=F(R_{ec}, G_{ec}, B_{ec})$ is applied to the RGB values $(R_{ec}, G_{ec}, B_{ec})$ at the position in the infra-red image data corresponding to the converted ocular region centre coordinates $(x_{ec}, y_{ec})$ to obtain the temperature Tc(t) (step S23). The forehead region coordinates $(x_{fh1}, y_{fh1})$, $(x_{fh2}, y_{fh2})$, $(x_{fh3}, y_{fh3})$ and so on are converted into the infra-red image data coordinate system (step S24). Then, the conversion $Tf(t)=F(R_{fn},G_{fn},B_{fn})$ is applied to the RGB values $(R_{fn},G_{fn},B_{fn})$ at the position in the infra-red image data surrounded by the converted forehead region coordinate group to obtain the temperature Tf(t) (step S25). Afterward, the formula core body temperature $Td(t)=\alpha \times Tf(t)-\beta \times Tc(t)$ is applied in step S26 to obtain the core body temperature Td(t).

According to the above-described Embodiment, temperature information obtained without contact is used to detect temperatures of an ocular region and a forehead region. A change from the normal temperature of the forehead region is then used, while accounting for the effect of environmental temperature as per the ocular region temperature change, to estimate drowsiness from temperature transitions. As such, the drowsiness estimation is enabled at an early stage without encumbering the user with sensors, and various services can thus be provided. For application to preventing the user from falling asleep at the wheel, drowsiness estimation performed before dozing enables an awakening warning to be made at an early stage.

Embodiment 2

In Embodiment 1, the forehead region temperature has a strong causal relationship with the core body temperature. Thus, the forehead region temperature Tf(t) is corrected using Tc(t) to obtain the core body temperature. However, areas having a great causal relationship with the core body temperature are not limited to the forehead region. The causal relationship with the core body temperature is also achievable with various other areas. Specifically, the skin over the nose bone and masseter muscle also has a causal relationship with the core body temperature, as described in Patent Literature 1. In the present Embodiment, the portion serving as a basis for detecting the core body temperature is not limited (to the forehead region) as in Embodiment 1. Instead, various candidates for core body temperature calculation are extracted from the face region and an appropriate base for core body temperature detection is selected from among temperatures of the candidates.

However, despite multiple areas being measured and used as the basis for calculating the core body temperature, some areas having no causal relationship to the core body temperature must be excluded from the calculation. In the present Embodiment, the drowsiness estimation device 100 is provided with a component for detecting areas having no causal relationship to the core body temperature, and such portions detected by the drowsiness estimation device 100 are excluded form core body temperature calculation.

Figure 9:
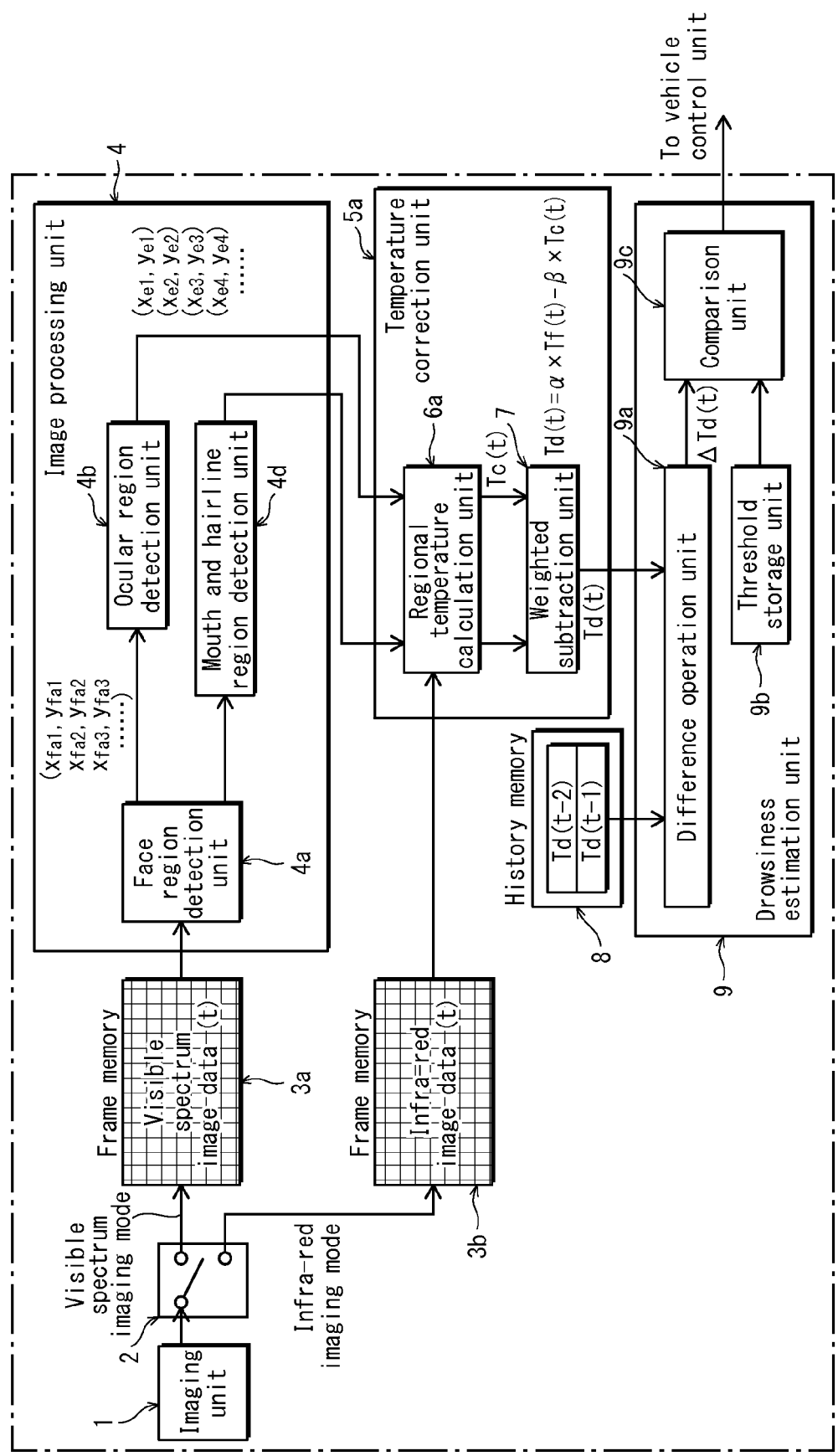
FIG. 9 shows the configuration of the drowsiness estimation device pertaining to Embodiment 2.

The configuration having the above-described improvements is illustrated by FIG. 9. FIG. 9 shows the configuration of the drowsiness estimation device pertaining to Embodiment 2. As shown, the components of Embodiment 1 serve as the base, and components differing from those of Embodiment 1 are substituted for the previous components. Specifically, the forehead region detection unit 4c is replaced by a mouth and hairline region detection unit 4d, and temperature correction unit 5 is replaced by temperature correction unit 5a.

The mouth and hairline region detection unit 4d detects a mouth region as being an area within the face region detection unit that is lower than the ocular region, and detects a hairline region as being an area within the face region that has different visual characteristics from the rest of the face region and is higher than the ocular region.

The regional temperature calculation unit 6a receives a coordinate group specifying the face region and a coordinate group specifying the mouth and hairline regions. These coordinate groups are then used to define a forbidden region as the ocular region and the mouth and hairline region. Afterward, a position is selected that is within a region outlined by the coordinate group defining the face region, is not in the forbidden region, and is a plausible candidate for core body temperature, and pixel values of pixels at the selected position are converted into temperature. Also, when coordinates specifying the ocular region centre are received, the pixel values of pixels at the ocular region centre are also converted into temperature.

This concludes the description of the new components (i.e., the mouth and hairline region detection unit 4d and the regional temperature calculation unit 6a). The following describes the operations of existing components that are deeply connected to the mouth and hairline region detection unit 4d.

As in Embodiment 1, the temperature correction unit 5a corrects the temperature of a candidate for core body temperature calculation using the ocular region centre temperature.

The drowsiness estimation unit 9 detects drowsiness by calculating a change over time in the temperature of the candidate region, as corrected using the ocular region temperature, and determining that drowsiness has occurred when the change is decreasing and the range of decrease exceeds a predetermined threshold. A drowsiness estimation result is then output.

According to the above-described configuration, the ocular region, which is prone to influencing the core body temperature, is defined as a forbidden region along with a mouth and hairline region. This enables other portions of the face region to be selected as candidates for core body temperature calculation, provided that these portions are not in contact with the forbidden region. Various portions of the face region, excluding the ocular region, the mouth region, and the hairline region, are usable as the bases for core body temperature calculation. As such, higher reliability is imparted to the drowsiness estimation, in comparison to the case where the core body temperature is based only on the forehead.

Embodiment 2 Application

This application example discusses a drowsiness estimation device equipped with the forehead region detection unit 4c described in Embodiment 1 as well as the mouth and hairline region detection unit 4d described in Embodiment 2.

Figure 10:
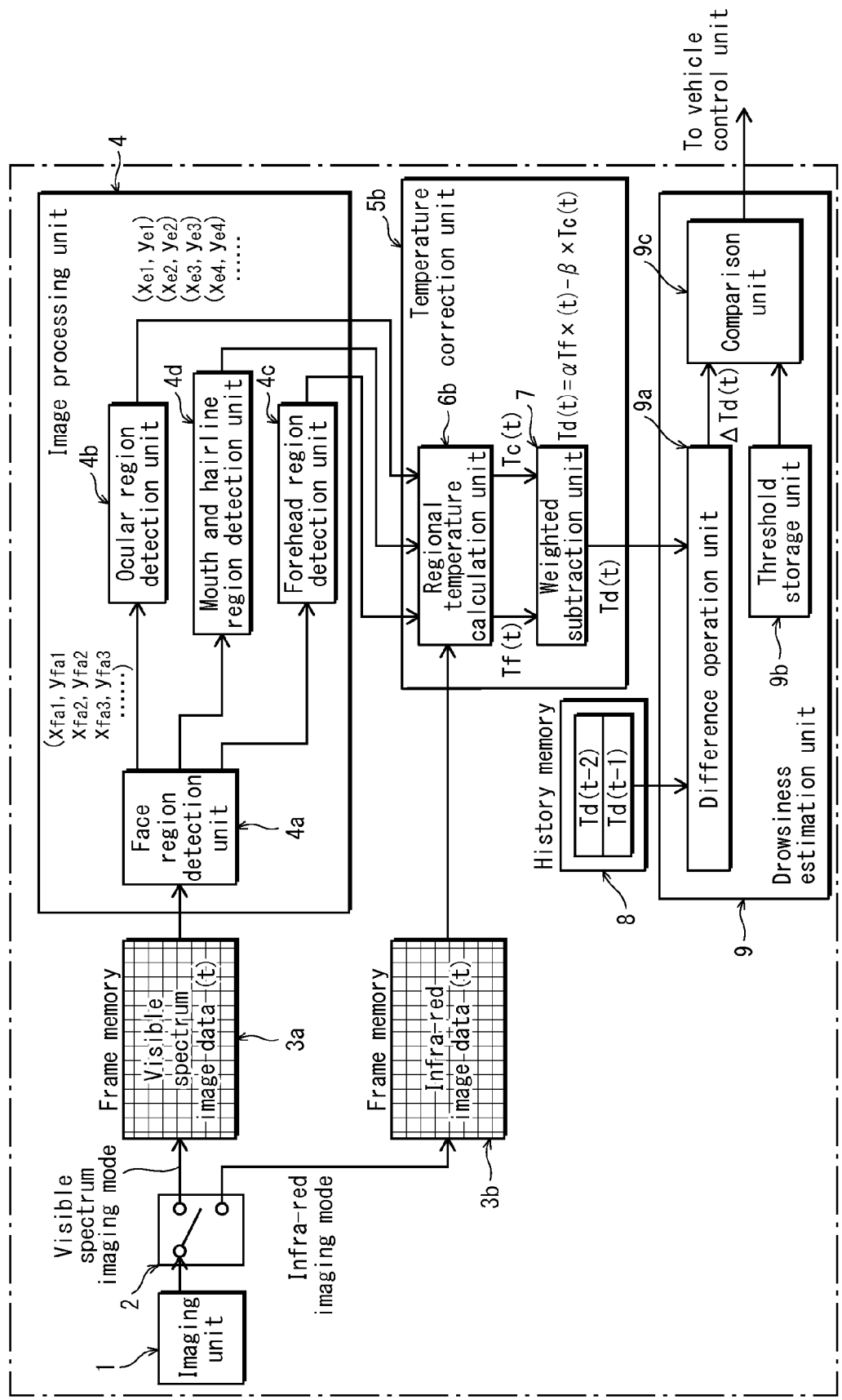
FIG. 10 shows the configuration of the drowsiness estimation device pertaining to the Embodiment 2.

FIG. 10 shows the configuration of the drowsiness estimation device pertaining to the Embodiment 2 application example. As shown, the image processing unit 4 includes the forehead region detection unit 4c and the mouth and hairline region detection unit 4d.

The forehead region detection unit 4c detects the forehead region, and the mouth and hairline region detection unit 4d detects the mouth and hairline. The regional temperature calculation unit 6b selects a target for temperature detection as one of the forehead detected by the forehead region detection unit 4c and a region of the face region excluding the ocular region, the mouth region, and the hairline region.

Also, the temperature correction unit 5 and the regional temperature calculation unit 6 of FIG. 2 are replaced by a temperature correction unit 5b and a regional temperature calculation unit 6b. The temperature correction unit 5b includes the regional temperature calculation unit 6b. The regional temperature calculation unit 6b obtains the core body temperature in two varieties, namely core body temperature 1 obtained by correcting the forehead region temperature Tf using the ocular region centre temperature Tc, and core body temperature 2 obtained by correcting the temperature of a region in the face region excluding the ocular region, the mouth region, and the hairline region using the ocular region centre temperature.

The drowsiness estimation unit 9 performs drowsiness estimation using both core body temperatures 1 and 2, and takes actions such as issuing a warning or making an outside notification when drowsiness is detected in either one.

Embodiment 3

In Embodiment 1, a temperature detected in the forehead region is uses as a parameter for drowsiness estimation. In contrast, the present Embodiment pertains to improving drowsiness estimation based on a measured value from a contact sensor worn on the user's body.

Figure 11:
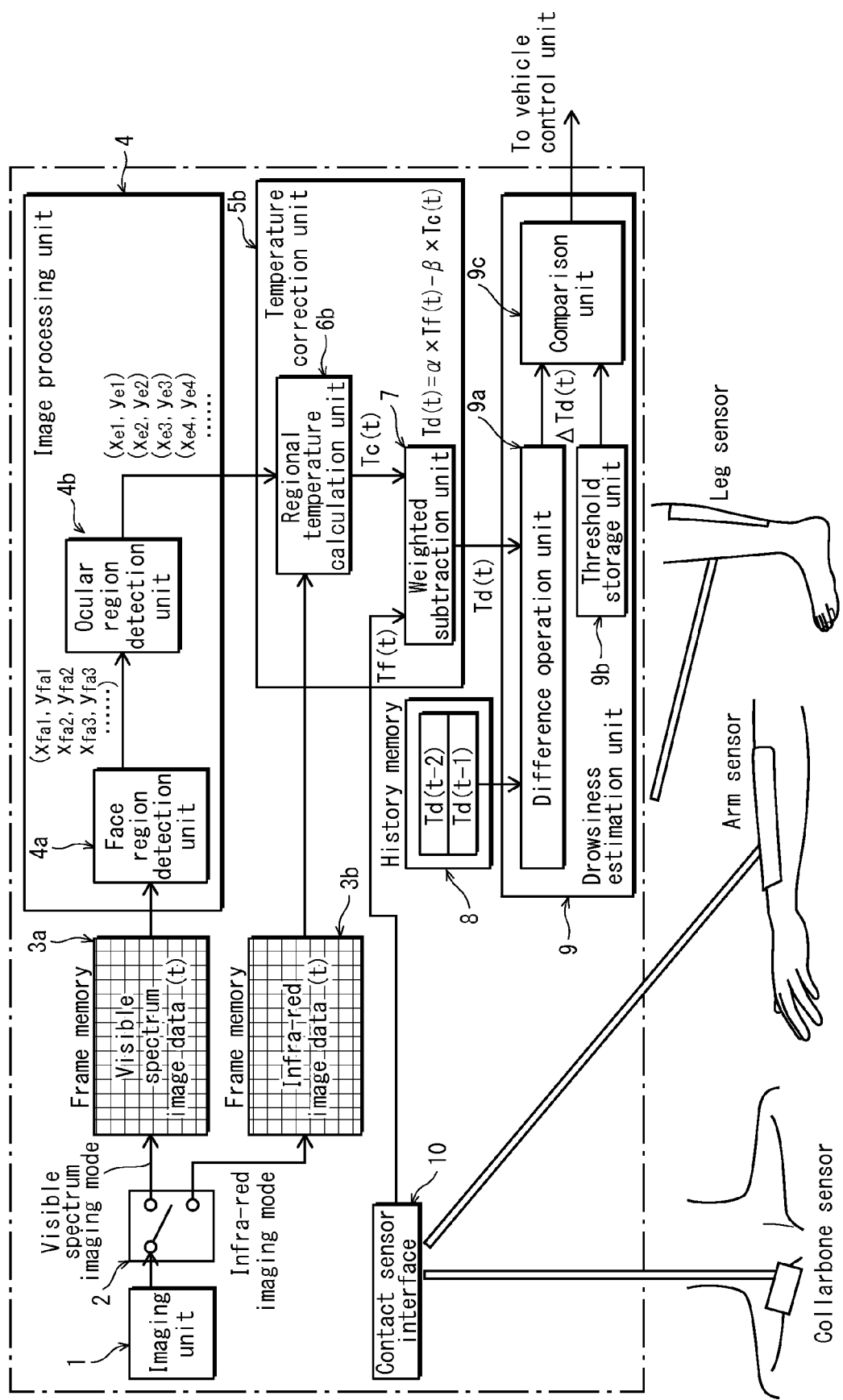
FIG. 11 shows the configuration of the drowsiness estimation device pertaining to Embodiment 3.

The configuration having the above-described improvements is illustrated by FIG. 11. FIG. 11 shows the configuration of the drowsiness estimation device pertaining to Embodiment 3. As shown, the components of Embodiment 1 serve as the base, differing in that the forehead region detection unit 4c and the mouth and hairline region detection unit 4d are absent. Instead, a contact sensor interface 10 is present.

The contact sensor interface 10 receives input of a body temperature, which is a measured value from the contact sensor on the user's body, and outputs it to the weighted subtraction unit 7. The contact sensor is worn on the collarbone, on the back of the arm, and on the back of the leg. As described in Non-Patent Literature 3, a measured value from a sensor worn on the collarbone is defined as a proximal temperature. An average value of measurements from the sensors worn on the back of the arm and on the back of the leg is defined as a distal temperature. The proximal and distal temperatures are strongly correlated with biological rhythms. Specifically, a large difference between the proximal and distal temperatures indicates drowsiness. As such, given that drowsiness occurs when the difference between the proximal and distal temperatures is greater than a predetermined threshold, a determination to the effect that the user is drowsy may be made in such cases.

The following describes the operations of existing components that are deeply connected to the new components. The weighted subtraction unit 7 uses the temperature detected at the ocular region centre to correct the difference between the proximal and distal temperatures as measured by the input to the contact sensor interface 10 and cancel environmental effects thereon. This enables more accurate measurement of the proximal and distal temperatures.

According to the above-described configuration, measurement values from a contact sensor worn on the user's body are used as the basis for drowsiness estimation. The temperature calculated from the infra-red image data is applied as a correction to the measured value from the contact sensor. As such, the drowsiness estimation is performed with higher precision than in cases where all needed parameters are obtained from the infra-red image data.

Embodiment 4

Figure 12:
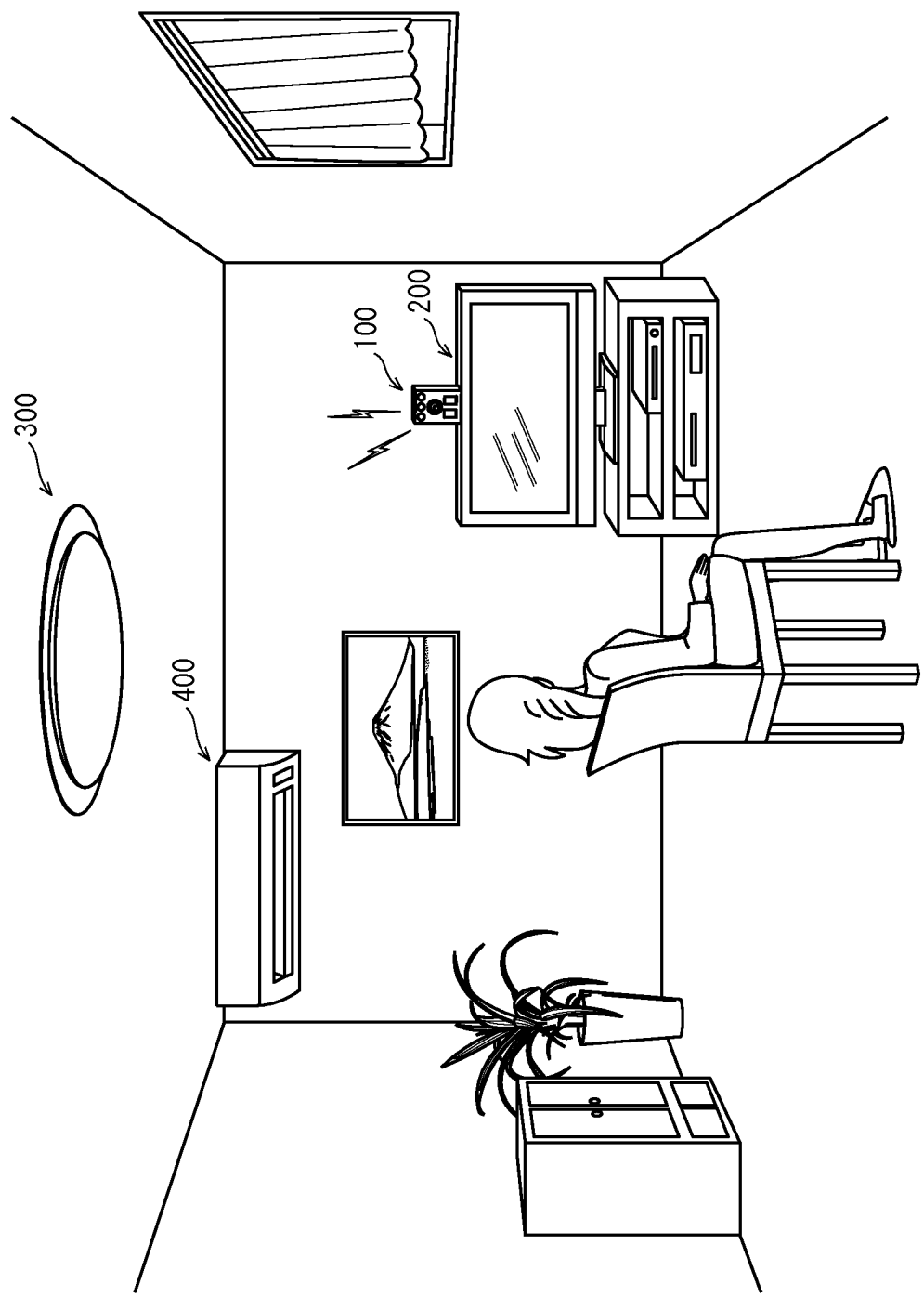
FIG. 12 illustrates a drowsiness estimation device mounted indoors for appliance control.

Embodiment 1 describes a vehicle-mounted drowsiness estimation device. However, the present Embodiment pertains to a drowsiness estimation device used for indoor appliance control. FIG. 12 illustrates a drowsiness estimation device mounted indoors for appliance control. As shown, the drowsiness estimation device 100 is mounted on top of a television 200, and is able to image a user watching the television 200. The drowsiness estimation device 100 calculates the core body temperature from captured visible spectrum and infra-red images, and performs drowsiness estimation according to the calculated core body temperature. When the above-described transition period is detected, a notification to such effect is made to the television 200, to a lighting device 300, and to an air conditioner 400.

Upon receiving the transition period notification from the drowsiness estimation device 100, the television 200 performs control such as reducing the volume or switching the power off.

Similarly, upon receiving the transition period notification from the drowsiness estimation device 100, the lighting device 300 performs control such as dimming the light.

Likewise, upon receiving the transition period notification from the drowsiness estimation device 100, the air conditioner 400 performs control such as increasing the indoor temperature, reducing wind intensity, and entering a night mode.

According to the above configuration, a more comfortable environment is provided to the user by decreasing television volume and lighting brightness, and by changing the room temperature, upon detecting drowsiness in the user.

Embodiment 5

In Embodiment 1, the camera 101 is both a visible spectrum and infra-red spectrum camera capable of capturing a visible spectrum image and an infra-red image with a single capture system. In the present Embodiment, drowsiness estimation device 100 replaces the camera 101 with a visible spectrum camera 102 for capturing a visible spectrum image and an infra-red camera 103 for capturing an infra-red image.

Here, the imaging unit 1 uses the visible spectrum camera 102 and the infra-red camera 103 at the predetermined time intervals where the visible spectrum and infra-red camera 101 had been used to perform two image captures, at visible spectrum wavelengths and infra-red wavelengths, respectively, and thus obtains visible spectrum image data and infra-red image data.

The visible spectrum camera 102 and the infra-red camera 103 provided within the drowsiness estimation device 100 alter the appearance of the subject's body in captured images according to the positional relationship between the cameras. Specifically, when the visible spectrum camera 102 and the infra-red camera 103 are arranged so as to neighbour each other, the respective images of the subject are offset horizontally. Also, when the visible spectrum camera 102 and the infra-red camera 103 are arranged one above the other, the respective images of the subject are offset vertically.

Typically, the infra-red image data has lower resolution than the visible spectrum image data.

In the present Embodiment, the regional temperature calculation unit 6b of the temperature correction unit 5b receives coordinate derivatives from the ocular region detection unit 4b, the forehead region detection unit 4c, and the mouth and hairline region detection unit 4d, and performs coordinate conversion on these visible spectrum image data-derived coordinates to obtain infra-red image data coordinates.

FIGS. 13A-13C illustrate coordinate conversion when the visible spectrum camera 102 and the infra-red camera 103 of the drowsiness estimation device 100 are aligned horizontally. FIG. 13A shows a perspective view of the drowsiness estimation device 100. As shown, the visible spectrum camera 102 and the infra-red camera 103 are aligned horizontally. FIG. 13B illustrates the visible spectrum image and the infra-red image. The infra-red image has lower resolution, and thus appears smaller. Given that the visible spectrum camera 102 and the infra-red camera 103 are aligned horizontally, the visible spectrum image and the infra-red image are horizontally offset by the value of offsetX.

The coordinate groups handed over by the ocular region detection unit 4b, the forehead region detection unit 4c, and the mouth and hairline region detection unit 4d, i.e., the coordinate group in the visible spectrum image data coordinate system, include given coordinates (Xv,Yv). Also, (Xi,Yi) are given coordinates in the infra-red image data coordinate system.

FIG. 13C indicates a formula for computing (Xi,Yi) from (Xv,Yv). The formula reads Xi=(infra-red image horizontal pixels/visible spectrum image horizontal pixels)×Xv+OffsetX, Yi=(infra-red image vertical pixels/visible spectrum image vertical pixels)×Yv.

Here, offsetX is the horizontal offset between the respective positions of the visible spectrum camera and the infra-red camera, indicating how far the X-coordinate origin of the infra-red image data coordinate system is located to the left or right of the visible spectrum image data coordinate system origin.

FIGS. 14A-14C illustrate coordinate conversion when the visible spectrum camera 102 and the infra-red camera 103 of the drowsiness estimation device 100 are aligned vertically. FIG. 14A shows a perspective view of the drowsiness estimation device 100. As shown, the visible spectrum camera 102 and the infra-red camera 103 are aligned vertically. FIG. 14B illustrates the visible spectrum image and the infra-red image. The infra-red image has lower resolution, and thus appears smaller. Given that the visible spectrum camera 102 and the infra-red camera 103 are aligned vertically, the visible spectrum image and the infra-red image are vertically offset by OffsetY. (Xv,Yv) are given coordinates in the visible spectrum image data coordinate system. Also, (Xi,Yi) are given coordinates in the infra-red image data coordinate system.

FIG. 14C indicates a formula for computing (Xi,Yi) from (Xv,Yv). The formula reads Xi=(horizontal pixels in infra-red image/horizontal pixels in visible spectrum image)×Xv, Yi=(vertical pixels in infra-red image/vertical pixels in visible spectrum image)×Yv+OffsetY.

Here, offsetY is the horizontal offset between the respective positions of the visible spectrum camera and the infra-red camera, indicating how far the Y-coordinate origin of the infra-red image data coordinate system is located to the top or bottom of the visible spectrum image data coordinate system origin.

The offsets (i.e., offsetX and offsetY) are produced when the visible spectrum camera and the infra-red camera are mounted next to each other. Thus, appropriate offset values are beneficially selected by performing calibration in an installation process of the drowsiness estimation device 100. Also, an appropriate value a vertical-to-horizontal pixel ratio by which Xv and Yv should be multiplied is also beneficially obtained through calibration.

Calibration is performed as follows. First, the ocular region detection unit 4b detects the ocular centre region in the visible spectrum image to obtain (Xv,Yv). Next, the ocular region detection unit 4b detects the ocular centre region in the infra-red image to obtain (Xi,Yi). Once (Xv,Yv) and (Xi,Yi) are acquired, then the above-described formulae are applied to obtain the horizontal/vertical pixel ratio for multiplying (Xv,Yv) and the offsets X and Y.

Some infra-red image coordinates must be detected during calibration. However, given that the infra-red image has lower resolution, this detection may have low precision. As such, input via interactive operation is desirable. That is, when the ocular region detection unit 4b detects the ocular region centre (Xv,Yv), the user may activate an interactive operation mode and specify the location of (Xi,Yi) corresponding to (Xv,Yv) in the infra-red image. Specifying (Xi,Yi) in this way enables the horizontal/vertical pixel ratio for multiplying (Xv,Yv) and the offsets X and Y to be derived from (Xv,Yv) and (Xi,Yi).

As described in Embodiment 1, a single camera may be equipped to perform visible spectrum imaging as well as infra-red imaging. In such a case, the values of OffsetX and OffsetY are zero. This is because, when a single camera captures the visible spectrum image and the infra-red image, no offset in the position of the subject relative to the camera installation position can possibly occur.

DISCUSSION

In the above-described Embodiments, an optimal Embodiment has been described. However, further improvements are also possible in connection with the following technical topics. Each of the Embodiments described above may be freely combined with the improvements and modifications, no limitation being intended by the Embodiments.

(Infra-Red Image Data)

In the above-described Embodiments, the infra-red image data captured in the infra-red capture mode are surface body temperature distribution data. However, this merely represents the intent that the infra-red image data be captured in the same imaging system as the image data visible spectrum image data. Provided that a correlation is defined between the temperature distribution of the user's body and coordinates, surface body temperature distribution data other than the infra-red image may be used.

(Necessary Components of Drowsiness Estimation Device 100)

When the drowsiness estimation device 100 is used in combination with another device, the configuration of the drowsiness estimation device 100 may omit the imaging system and frame memory, so as to comprise only the image processing unit 4 through the drowsiness estimation unit 9. The imaging unit 1 is provided in order to obtain the visible spectrum image data and the infra-red image data. Thus, having another device used with the drowsiness estimation device 100 provided these is sufficient.

(Device Configuration)

In Embodiment 1, the drowsiness estimation device 100 is described as a standalone device mounted within a vehicle. Alternatively, the drowsiness estimation device 100 may be integrated with a vehicle navigation device or audio-visual device. In Embodiment 3, the drowsiness estimation device may also be integrated with the television, the lighting device, or the air conditioner.

(Drowsiness Estimation Device Production)

The drowsiness estimation device 100 may be produced as a device equipped with a videophone function, such as a television, personal computer, smart phone, or tablet terminal. The videophone function must be able to transmit video captured by the device to another party, and the user is thus able to view a self-image.

(Visible Spectrum Image Recording)

For each measurement time, the visible spectrum image may be encoded to obtain a video stream. The core body temperature at each measurement time may then be associated with the video stream and recorded on a recording medium. Recording the core body temperature at each measurement time in association with the video stream enables the drowsiness estimation device 100 to act as a biological rhythms recorder.

(Network Applications)

The drowsiness estimation device may be connected to an imaging device via a network. In such a case, the drowsiness estimation device receives measurement images (i.e., the visible spectrum image data and the infra-red image data) from the camera of a display device connected via the network, and performs drowsiness estimation therewith. The estimation results are then output to an external device which executes processing in response to the drowsiness.

(Multi-User Application)

The drowsiness estimation device 100 may perform drowsiness estimation using data obtained by imaging a plurality of users and calculating the core body temperature in association with a plurality of paired visible spectrum and infra-red images. An alert may be issued if a user among the plurality of imaged users is dozing. Thus, for instance, a corporation employing a plurality of operators is able to use a visible spectrum image from a computer-mounted camera or a vehicular camera with an infra-red image to determine whether any of the operators are dozing. In this situation, a plurality of visible spectrum and infra-red images must be processed. As such, a cloud network server (i.e., a cloud server) capable of processing visible spectrum and infra-red image data on a large scale beneficially operates the drowsiness estimation device 100. Upon being instructed to begin drowsiness estimation on the cloud network, a hypervisor initialises the operating system of the cloud server. Once the operating system is initialised, a local business intranet loads an application performing the processing of the image processing unit 4, the temperature correction unit 5, and the drowsiness estimation unit 9 onto the cloud server. This loading causes the processing described in Embodiments 1 through 5 to be performed on the large-scale data.

(Measurement Period)

The visible spectrum image may be one among individual visible spectrum images obtained using video image capturing, or may be one among individual visible spectrum images captured using still image capturing. When the visible spectrum images are obtained using video image capturing, the core body temperature measurement period is a display period used when playing back the video image. For example, the measurement period is 1/23.976 s when the display frequency is 23.976 Hz, 1/59.94 s when the display frequency is calculated by field conversion as 59.94 Hz, and 1/50 s when the display frequency is calculated by field conversion as 50 Hz.

When the visible spectrum images are obtained by still image capturing, the core body temperature measurement period is defined according to a timer setting of the drowsiness estimation device. For example, when the drowsiness estimation device timer is set to 5 s, then the drowsiness estimation device performs imaging every five seconds, such that core body temperature is obtained at five-second intervals.

(Ocular Region Detection by Shape Pattern Dictionary)

The ocular region detection unit 4b may register eyelid shape patterns indicating various eyelid shapes in a detection dictionary, and use the detection dictionary in ocular region detection. Specifically, the ocular region detection unit performs feature extraction on the visible spectrum image to extract an edge pixel group at a position of the visible spectrum image where the pixel values greatly differ from their surroundings. A region of the edge pixel group matching a shape pattern registered in the detection dictionary is detected as the ocular region. Also, registering a face outline pattern, a forehead outline pattern, and so on in the detection dictionary enables the face region and forehead region to be similarly detected.

(Ocular Region Detection by Colour Distribution)

The ocular region detection may also be performed by detecting a region that is surrounded by a colour region having the same colouring as the skin in the face region but does not, itself, have the colouring of the skin. Then, evaluation is performed regarding distribution rules such as the positional relationships in the face above and below the pair of ocular regions and the lateral arrangement of the pair of ocular regions, the difference in surface area between the pair of ocular regions, and the colour distribution within the pair of ocular regions. According to this evaluation, the ocular region for both eyes is estimated as being the pair of ocular regions determined as being most appropriate.

(Coordinate Conversion Unification)

In Embodiment 1, the coordinate conversion formula varied according to whether the visible spectrum camera 102 and the infra-red camera 103 where arranged horizontally or vertically, or were combined into a camera 101 that is both a visible spectrum and infra-red spectrum camera. However, a unified formula may also be used for coordinate conversion. That is, the following formula may be used for coordinate conversion regardless of whether the infra-red camera 103 is beside, above, below, or combined into a camera 101 that is both a visible spectrum and infra-red spectrum camera.

$$Xi = (\text{horizontal pixels in infra-red image/horizontal pixels in visible spectrum image}) \times Xv + \text{Offset}X$$

$$Yi = (\text{vertical pixels in infra-red image/vertical pixels in visible spectrum image}) \times Yv.$$

This is because the visible spectrum image and the infra-red image have a minor offset in the vertical and horizontal directions. Specifically, the above-given formula should be used regardless of camera arrangement, in consideration of the difference in resolution between the visible spectrum image and the infra-red image/

(Follow-Up Imaging)

An imaging sensor, such as a focus lens movable along an optical axis, or an imaging optical system adjusting an amount of light in accordance with a driving control, may perform follow-up imaging of the user's face region. In such a case, the imaging sensor inputs video that includes the user's face to a video processing unit, and the face region detection unit receives all input of video data imaged by the imaging unit.

(Infra-Red Camera Configuration)

The infra-red camera may be configured as a housing containing an infra-red lens group and an infra-red imaging element arranged in an imaging plane of the infra-red lens group. The housing is configured with a window through which the infra-red lens group faces the subject. The infra-red imaging element is configured as a plurality of thermo-sensitive resistors arranged in a one-dimensional or two-dimensional array, generating the infra-red image data by detecting an amount of infra-red light received by the thermo-sensitive resistors.

(Infra-Red Opacity and Transmittance by Filter)

Normally, the optical filter of a capture device is configured to be opaque to infra-red wavelengths. The camera 101, which is both a visible spectrum and infra-red spectrum camera, controls switching regarding whether or not to be opaque to infra-red wavelengths. Thus, the visible spectrum image data and the infra-red image data are respectively acquired by switching between the visible spectrum capture mode and the infra-red capture mode. First of all, the visible spectrum image data are captured in the visible spectrum capture mode by switching to a filter that is opaque to infra-red. Next, image data are obtained in the infra-red capture mode from individual pixels in the visible spectrum and in infra-red by switching to a filter having transmittance to infra-red and visible spectrum light. After obtaining such image data, a difference between each pixel of these image data and the visible spectrum image data obtained in the visible spectrum capture mode is computed and the difference values are used as pixel values of the infra-red image data. Through this process, filters in a normal imaging device are usable for obtaining the visible spectrum image data and the infra-red image data.

(Switching Modes by Colour Filters)

The camera 101 that is both a visible spectrum and infra-red spectrum camera may be improved using colour filters disposed in front of the imaging element and switching between the visible spectrum capture mode and the infra-red capture mode to capture the visible spectrum image data and the infra-red image data. The colour filters are provided in a plurality of types, and have transmittance to specific wavelengths so as to allow electromagnetic waves of specific wavelengths to pass. The specific-wavelength filters include at least an R-filter having transmittance to red-component electromagnetic wavelengths, a B-filter having transmittance to blue-component electromagnetic wavelengths, a G-filter having transmittance to green-component electromagnetic wavelengths, and I-filter filter having transmittance to infra-red wavelengths. The R-, G-, B-, and I-filters are provided as a plurality of filter groups arranged in a matrix having a predetermined number of rows and columns. The filter groups are arranged in a matrix such that the I-filter neighbours the R-filter and the B-filter. According to this configuration, the visible spectrum capture mode uses the R-, G-, and B-filters while the infra-red capture mode uses the I-filter. As such, the visible spectrum image data are captured in the visible spectrum capture mode and the infra-red image data are captured in the infra-red capture mode.

(Range of Formulae and Calculations)

The formulae used to compute the core body temperature and to derive the core body temperature from the infra-red image data do not represent mathematical concepts, and are merely intended to indicate mathematical calculations executed by a computer. Obviously, improvements necessary to execution by a computer may be freely performed. For example, a saturate calculation or a conversion to positive values may be applied to the numerical values in order to treat said values as integers, as fixed point values, or as floating point values. Furthermore, in each of the Embodiments, the mathematical processing and computations based on the mathematical formulae are realised by a multiplier in read-only memory (hereinafter, ROM) using a constant ROM value. The constant ROM contains a value computed in advance by taking the product of a multiplier and a constant. For example, when the multiplier has a 16-bit length, then the multiplier is divided into four 4-bit portions, and the product of the integer and each of the 4-bit portions, i.e., a multiple of a constant 0 through 15, is stored in the aforementioned constant ROM. The product of the above-described 4-bit portions and the 16-bit constant has a length of 20 bits. The four constants are thus stored at the same address, which is one word having a length of 20×4=80 bits. As described above, the calculations are performed by a multiplier in ROM. Thus, the calculations and computations described in the present description do not represent pure arithmetic calculations but instead include reading, from a recording medium, values obtained from the results of calculations stored on the recording medium or in ROM.

(Integrated Circuit Realisation)

The image processing unit 4 and the temperature correction unit 5 are semiconductor integrated circuits embedded within the device. The image processing unit 4 and the temperature correction unit 5 may also each be a system LSI packaged for improved density on the substrate. The system LSI may each be realised as a plurality of individual bare chips mounted on a high-density substrate, or may be a multi-chip module in which a plurality of bare chips are packaged so as to have the appearance of a single LSI. The integrated circuit architecture includes the following: (1) a front-end processing circuit that is a pre-programmed DMA master circuit or similar, executing overall stream processing; (2) a signal processing circuit made up of a SIBD processor or similar, executing overall signal processing; (3) a back-end circuit performing overall operations of pixel processing and image compositing, resizing, image format conversion, and audio-visual output; (4) a media interface circuit that is an interface with a drive or network; and (5) a memory controller circuit that is a slave circuit for memory access, executing reading and writing of packets and data according to a request from the front-end unit, the signal processing unit, and the back-end unit. In terms of package type, applicable types for a system LSI include a quad flat package (hereinafter, QFP) and a pin grid array (hereinafter, PGA). A QFP is a system LSI mounted with pins at the four sides thereof. A PGA is a system LSI mounted using a multitude of pins at the bottom face thereof.

As for the realisation of the integrated circuit, any of the following may be added as internal processing components: a conversion circuit converting a pixel group of the visible spectrum image data or the infra-red image data into a desired format; a cache memory temporarily storing the pixel group of the visible spectrum image data or infra-red image data; a buffer memory performing a data transfer speed adjustment; an initialisation circuit reading a required program from ROM into RAM when power is initially supplied, thus initialising the integrated circuit; a power supply circuit supplying electric power according to the state of a histogram; a program manager managing a plurality of programs as task programs in an MPU of a control unit and scheduling the programs according to a priority; and an interrupt handler generating an interrupt signal in response to external conditions such as a reset or a power supply interruption.

Embodiment as a Program

The present disclosure may be configured as a program module receiving a visible spectrum image data index and an infra-red image data index as arguments and performing a call to a desired application programing interface to determine the drowsiness of the user, and return a determined value. Program code making up such a program module, i.e., program code causing a computer to perform the processing indicated in the main routine of FIG. 7 and the subroutine of FIG. 8, is created using the following process. First, a software developer uses a programming language to write a source program for realising the flowcharts and functional elements of the Embodiments. The software developer writes the source program in accordance with the syntax of a programming language, using class structures, variables, array variables, and calls to outside functions, such that the source program embodies the functions of the components and flowcharts.

The resulting source program is then passed to a complier as a file. The compiler generates an object program by translating the source program.

The translation by the compiler involves steps of syntax analysis, optimization, resource allocation, and code generation. Syntax analysis is parsing the syntax and meaning of the source program through character analysis, thus conversing the source program into an intermediate program. Optimization is performing operations on the intermediate program to convert the program into basic blocks, and to analyse the control flow and data flow. Resource allocation is allocating variables in the intermediate program to a register or memory usable by a processor targeted thereby, so as to supply the appropriate resources for a processer targeted by an instruction set. Code generation is converting intermediate instructions in the intermediate program into program code to obtain the object program.

The object program thus generated is made up of one or more pieces of program code that cause a computer to execute individual steps of the flowcharts described in the above Embodiments, or to realise operations corresponding to the individual functional components. The program code is the processor's native code, Java™ bytecode, or some other type of code. The steps may be executed through the program code in various ways. When a call to an external function is made to realise the steps, the program code is a call statement calling the appropriate function. Alternatively, when the program code itself realises a single step, each corresponding piece of code belongs to a separate object program. For a RISC processor in which types of instructions are limited, arithmetic calculation instructions, logical calculation instructions, branch instructions, and so on are combined to realise the steps of the flowcharts. When the object program is generated, the programmer places linkers thereto. A linker spatially allocates the object programs and the relevant library programs so as to link them as one and generate a load module. The load module so generated is intended to be read by a computer. The computer is thus made to execute the steps of the flowcharts and the functions of the components. The computer program is recorded on a non-volatile computer readable recording medium and distributed to a user.

INDUSTRIAL APPLICABILITY

The drowsiness estimation device is applicable to preventing drivers from falling asleep at the wheel. The device is also applicable to control of lighting brightness, television volume, and so on.

LIST OF REFERENCE SIGNS

1 Imaging unit
2 Switching unit
3a, 3b Frame memory
4 Image processing unit
4a Face region detection unit
4b Ocular region detection unit
4c Forehead region detection unit
4d Mouth and hairline region detection unit
5 Temperature correction unit
5a, 5b Temperature correction unit
6 Regional temperature calculation unit
6a, 6b Regional temperature calculation unit
7 Weighted subtraction unit
8 History memory
9 Drowsiness estimation unit
10 Contact sensor interface
9a Difference operation unit
9b Threshold storage unit
9c Comparison unit
100 Drowsiness estimation device
101 Camera (visible spectrum and infra-red spectrum camera)
102 Visible spectrum camera
103 Infra-red camera
200 Television
300 Lighting device
400 Air conditioner

The invention claimed is:

1. A drowsiness estimation device detecting a temperature parameter for a drowsiness estimation of a person subject to the drowsiness estimation, and performing the drowsiness estimation, the drowsiness estimation device comprising:
   acquisition circuitry acquiring visible spectrum image data obtained by capturing a plurality of images of the person with visible spectrum wavelengths, and surface body temperature distribution data obtained by measuring a temperature distribution of a body surface of the person;
   image processing circuitry specifying an ocular region center for the person by performing image processing on the visible spectrum image data; and
   correction circuitry detecting a temperature of the ocular region center in the surface body temperature distribution data for the person, and using the temperature of the ocular region center to apply a correction to the temperature parameter for the drowsiness estimation, wherein
   the correction to the temperature parameter is performed by multiplying the temperature parameter by a first weighting coefficient and the temperature of the ocular region center by a second weighting coefficient, and subtracting a weighted temperature of the ocular region center from a weighted temperature parameter.

2. The drowsiness estimation device of claim 1, wherein the image processing circuitry specifies the ocular region center by detecting an outline of a cornea in a face region of the person appearing in the visual spectrum image data, and specifying an arc center as indicated by the outline of the cornea.

3. The drowsiness estimation device of claim 1, wherein the temperature parameter is a body temperature in a forehead region within a face region of the person appearing in the visual spectrum image data, and
   the correction circuitry obtains the temperature parameter by detecting a forehead region temperature from the surface body temperature distribution data.

4. The drowsiness estimation device of claim 1, wherein the temperature parameter is a body temperature of a portion of a face region of the person appearing in the visual spectrum image data, excluding a mouth region and a hairline region, and
   the correction circuitry obtains the temperature parameter by detecting a portion temperature in the face region excluding the mouth region and the hairline region, from the surface body temperature distribution data.

5. The drowsiness estimation device of claim 1, wherein the surface body temperature distribution data is infra-red image data made up of a plurality of pixels and having a predetermined resolution, the pixels of the infra-red image data are in correspondence with pixels of the visible spectrum image data, and a color component luminance of each of the pixels of the infra-red image data indicates an amount of infra-red radiation emitted by a corresponding portion of the body surface of the person appearing in the visual spectrum image data.

6. The drowsiness estimation device of claim 5, wherein the visual spectrum image data and the infra-red image data differ in resolution, the image processing circuitry specifies the ocular region center using an X-coordinate or a Y-coordinate in a coordinate system of the visual spectrum image data, the correction circuitry applies a conversion to the X-coordinate or the Y-coordinate of the ocular region center and converts a pixel value from the infra-red image data at a converted X-coordinate or a converted Y-coordinate into a temperature, and the conversion applied by the correction circuitry involves multiplying the X-coordinate or the Y-coordinate of the ocular region center by a horizontal pixel ratio or a vertical pixel ratio of the visible spectrum image data and the infra-red image data, and then adding a horizontal offset or a vertical offset representing a cause of difference between a visible spectrum imaging system and an infra-red spectrum imaging system.

7. The drowsiness estimation device of claim 6, wherein the visible spectrum image data and the infra-red image data are obtained by capturing the images of the person at a plurality of imaging times in a measurement time slot, at each of the imaging times, the image processing circuitry specifies the ocular region center, the acquisition circuitry acquires the infra-red image data, and the correction circuitry applies the correction to the temperature parameter, and the drowsiness estimation is performed by comparing a corrected temperature parameter for a given measurement time to a past corrected temperature parameter for a past measurement time, and determining whether a downward trend is occurring and whether a span of the downward trend exceeds a predetermined threshold.

8. The drowsiness estimation device of claim 5, further comprising imaging circuitry that is switchable to one of a first mode of being transmissive to the visible spectrum wavelengths and opaque to infra-red wavelengths, and a second mode of being transmissive to the infra-red wavelengths and opaque to the visible spectrum wavelengths, wherein the visible spectrum image data and the infra-red image data are respectively obtained by switching between the first mode and the second mode.

9. The drowsiness estimation device of claim 1, wherein the temperature parameter for the drowsiness estimation is acquired by a contact sensor attached to an arm, a leg, and a collarbone of the person.

10. A drowsiness estimation method used by a drowsiness estimation device detecting a temperature parameter for a drowsiness estimation of a person subject to the drowsiness estimation, and performing the drowsiness estimation, the drowsiness estimation method comprising:

acquiring visible spectrum image data obtained by capturing a plurality of images of the person with visible spectrum wavelengths, and surface body temperature distribution data obtained by measuring a temperature distribution of a body surface of the person;

performing image processing on the visible spectrum image data by specifying an ocular region center for the person; and applying a correction to the temperature parameter for the drowsiness estimation by detecting a temperature of the ocular region center in the surface body temperature distribution data for the person, and using the temperature of the ocular region center to apply the correction, wherein the correction to the temperature parameter is performed by multiplying the temperature parameter by a first weighting coefficient and the temperature of the ocular region center by a second weighting coefficient, and subtracting a weighted temperature of the ocular region center from a weighted temperature parameter.

11. A computer-readable non-transitory recording medium on which one or more program codes are recorded for causing a computer to perform a drowsiness estimation of a person subject to the drowsiness estimation using a temperature parameter, by causing the computer to execute processing of:

acquiring visible spectrum image data obtained by capturing a plurality of images of the person with visible spectrum wavelengths, and surface body temperature distribution data obtained by measuring a temperature distribution of a body surface of the person;

performing image processing on the visible spectrum image data by specifying an ocular region center for the person; and applying a correction to the temperature parameter for the drowsiness estimation by detecting a temperature of the ocular region center in the surface body temperature distribution data for the person, and using the temperature of the ocular region center to apply the correction, wherein the correction to the temperature parameter is performed by multiplying the temperature parameter by a first weighting coefficient and the temperature of the ocular region center by a second weighting coefficient, and subtracting a weighted temperature of the ocular region center from a weighted temperature parameter.

* * * * *